(12) United States Patent
Kerr

(10) Patent No.: US 9,006,221 B2
(45) Date of Patent: Apr. 14, 2015

(54) METHOD OF MODULATING SHIP ACTIVITY

(75) Inventor: William G. Kerr, Syracuse, NY (US)

(73) Assignee: H. Lee Moffitt Cancer Center and Reserach Institute, Inc., Tampa, FL (US)

(*) Notice: Subject to any disclaimer, the term of this patent is extended or adjusted under 35 U.S.C. 154(b) by 0 days.

(21) Appl. No.: 13/085,824

(22) Filed: Apr. 13, 2011

(65) Prior Publication Data

US 2012/0178725 A1    Jul. 12, 2012

Related U.S. Application Data

(63) Continuation of application No. PCT/US2009/060457, filed on Oct. 13, 2009.

(60) Provisional application No. 61/104,883, filed on Oct. 13, 2008.

(51) Int. Cl.
*A01N 45/00* (2006.01)
*A61K 31/56* (2006.01)
*A61K 31/575* (2006.01)

(52) U.S. Cl.
CPC .................................... *A61K 31/575* (2013.01)

(58) Field of Classification Search
None
See application file for complete search history.

(56) References Cited

U.S. PATENT DOCUMENTS

| 7,691,821 B2 * | 4/2010 | Desponts et al. ............ 514/44 R |
| 7,713,945 B2 * | 5/2010 | Kerr ............................ 514/44 R |
| 8,163,710 B2 * | 4/2012 | Kerr ............................ 514/44 R |
| 2006/0106038 A1 * | 5/2006 | Bouscary et al. ......... 514/263.21 |
| 2006/0223749 A1 * | 10/2006 | Desponts et al. ............... 514/12 |

FOREIGN PATENT DOCUMENTS

WO   WO 02058622 A2 *   8/2002
WO   WO 2008068037 A1 *   6/2008

OTHER PUBLICATIONS

Gratwohl et al., "Hematopoietic stem cell transplantation for hematological malignancies in Europe," Leukemia, May 2003; 17(5):941-59.*
Patani et al., "Bioisosterism: A Rational Approach in Drug Design," Chem. Rev. 1996, 965, 3147-3176.*
O'Brien et al., Infections in Patients with Hematological Cancer: Recent Developments, American Society of Hematology, pp. 438-472 (2003).*
Jain et al. "PI 3-Kinase Activation in BCR/abl-Transformed Hematopoietic Cells Does Not Require Interaction of p85 SH2 Domains with p210 BCR/abl." Blood. (1996). vol. 88. No. 5. pp. 1542-1550.
Kosaka et al. "Stimulation of Mature Unprimed CD8+ T Cells by Semiprofessional Antigen-Presenting Cells in Vivo." J. Exp. Med. (1992). vol. 176. No. 5. pp. 1291-1302.
Lafferty et al. "The Allograft Response." Surg. Clin. North Am. (1986). vol. 66. No. 6. pp. 1231-1253.
Liu et al. "SHIP is a Negative Regulator of Growth Factor Receptor-Mediated PKB/Akt Activation and Myeloid Cell Survival." Genes & Development. (1999). vol. 13. No. 7. pp. 786-791.
Liu et al. "The Inositol Polyphosphate 5-Phosphatase Ship Is a Crucial Negative Regulator of B Cell Antigen Receptor Signaling." J. Exp. Med. (1998). vol. 188. No. 7. pp. 1333-1342.
MacDonald et al. "Cytokine Expanded Myeloid Precursors Function as Regulatory Antigen-Presenting Cells and Promote Tolerance through IL-10-Producing Regulatory T Cells." J. Immunol. (2005). vol. 174. No. 4. pp. 1841-1850.
McPherson et al. "PCR A Practical Approach." Oxford University Press. (1991). pp. Table of Contents-xvi.
Paraiso et al. "Induced SHIP Deficiency Expands Myeloid Regulatory Cells and Abrogates Graft-versus-Host Disease." J. Immunol. (2007). vol. 178. No. 5. pp. 2893-2900.
Prasad. "SHIP2 Phosphoinositol Phosphatase Positively Regulates EGFR-Akt Pathway, CXCr4 Expression, and Cell Migration in MDA-MB-231 Breast Cancer Cells." Int. J. Oncol. (2009). vol. 34. No. 1. pp. 97-105.
Prasad et al. "Phosphoinositol Phosphatase SHIP2 Promotes Cancer Development and Metastasis Coupled with Alterations in EGTF Receptor Turnover." Carcinogenesis. (2008). vol. 29. No. 1. pp. 25-34.
Prasad et al. "High Expression of Obesity-Linked Phosphatase SHIP2 in InvasiveBreast Cancer Correlates with Reduced Disease-Free Survival." Tumour Biol. (2008). vol. 29. No. 5. pp. 330-341.
Sambrook et al. "Molecular Cloning: A Laboratory Manual." Cold Spring Harbor Laboratory Press, Cold Spring Harbor, N.Y. 2d ed. (1989). pp. title page-xxi.
Shlomchik et al. "Prevention of Graft Versus Host Disease by Inactivation of Host Antigen-Presenting Cells." Science. (1999). vol. 285. No. 5426. pp. 412-415.
Wahle et al. "Inappropriate Recruitment and Activity by the Src HomologyRegion 2 Domain-Containing Phosphatase 1 (SHP1) Is Responsible for Receptor Dominance in the Ship-Deficient NK Cell." J. Immunol. (2007). vol. 179. No. 12. pp. 8009-8015.
Wang et al. "Influence of SHIP on the NK Repertiore and Allogenic Bone Marrow Transplantation." Science. (2002). vol. 295. No. 5562. pp. 2094-2097.
Yilmaz et al. "Pten Dependence Distinguishes Haematopoietic Stem Cells from Leukemia-Initiating Cells." Nature. (2006). vol. 441. No. 7092. pp. 475-482.
Yuan et al. "PI3K Pathway Alterations in Cancer: Variations on a Theme." Oncogene. (2008). vol. 27. No. 41. pp. 5497-5510.
Zhang et al. "PTEN Maintains Haematopoietic Stem Cells and Acts in Lineage Choice and Leukaemia Prevention." Nature. (2006). vol. 441. No. 7092. pp. 518-522.

(Continued)

*Primary Examiner* — Craig Ricci
*Assistant Examiner* — Jared D Barsky
(74) *Attorney, Agent, or Firm* — Michele L. Lawson; Michael M. McGaw; Smith & Hopen, P.A.

(57) ABSTRACT

A method of treating or preventing an immune disorder, such as graft versus host disease, in a subject. The method includes the administering a SHIP1 inhibitor, such as 3α-aminocholestane, to a subject in need of treatment. Thus, SHIP1 inhibitors taught herein represent a novel class of small molecules that have the potential to enhance allogeneic transplantation, boost innate immunity and improve the treatment of hematologic malignancies.

1 Claim, 25 Drawing Sheets

(56) References Cited

OTHER PUBLICATIONS

Innis et al. "PCR Protocols: A Guide to Methods and Applications." Academic Press, San Diego, Calif. (1990). pp. title page-x.
Tu et al. "Embryonic and Hematopoietic Stem Cells Express a Novel SH2-Containing Inositol 5'-Phosphatase Isoform that Partners with the Grb2 Adapter Protein." Blood. (2001). vol. 98. pp. 2028-2038.
Freeburn et al. 2002. Evidence that SHIP-1 contributes to phosphatidylinositol 3,4,5-trisphosphate metabolism in t lymphocytes and can regulate novel phosphoinositide 3-kinase effectors. J. Immunol. vol. 169. pp. 5441-5450.
Horn et al. 2004. Restoration of SHIP activity in a human leukemia cell line downregulates constitutively activated phosphatidylinositol 3-kinase/Akt/GSK-3 beta signaling and leads to an increased transit time through the G1 phase of the cell cycle. Leukemia. vol. 18. pp. 1839-1849.
International Report on Patentability for PCT application No. PCT/US2009/060457 with an international filing date of Oct. 13, 2009.
Ausubel et al., "Short Protocols in Molecular Biology." (1999) 4th Ed. John Wiley & Sons, Inc. pp. title page-xvi.
Brauweiler et al. "Differential Regulation of B Cell Development, Activation, and Death by the Src Homology 2 Domain-containing 5' Inositol Phosphatase (SHIP)." J. Exp. Med. (2000). vol. 191. No. 9. pp. 1545-1554.
Collazo et al. "SHIP Limits Immunoregulatory Capacity in the T-Cell Compartment." Blood. (2009). vol. 113. pp. 2934-2944.
Drees et al. "Competitive Fluorescence Polarization Assays for the Detection of Phosphoinositide Kinase and Phosphatase Activity." Comb. Chem. High Throughput Screen. (2003). vol. 6. No. 4. pp. 321-330.
Franke et al. "Direct Regulation of the Akt Proto-Oncogene Product by Phosphatidylinositol-3,4-bisphosphate." Science. (1997). vol. 275. pp. 665-668.
Murray. "Gene Transfer and Expression Protocols." The Humana Press Inc., Clifton, N.J. pp. 109-128.
Ghansah et al. "Expansion of Myeloid Suppressor Cells in SHIP-Deficient Mice Repress Allogenic T Cell Responses." J. Immunol. (2004). vol. 173. No. 12. pp. 7324-7330.
Guthrie et al. "Guide to Yeast Genetics and Molecular Biology, Methods in Enzymology, vol. 194." Academic Press, Inc., (1991). pp. table of contents-ix.
Hazen et al. "SHIP is Required for a Functional Hematopoietic Stem Cell Niche." Blood. (2009). vol. 113. No. 13. pp. 2924-2933.
Helgason et al. "Targeted Disruption of SHIP leads to Hemopoietic Perturbations, Lung Pathology, and a Shortened Lifespan." Genes & Development. (1998). vol. 12. No. 11. pp. 1610-1620.
Ivetac et al. "Regulation of PI(3)K/Akt Signalling and Cellular Transformation by Inositol Polyphosphate 4-Phosphatase-1" EMBO Rep. (2009). vol. 10. No. 5. pp. 487-493.
Fuhler et al., Therapeutic Potential of SH2 Domain-Containing Inositol-5—Phosphatase 1 (SHIP1) and SHIP2 Inhibition in Cancer, Molecular Medicine, 2012 vol. 18, pp. 65-75.
Hamilton et al., Role of SHIP in cancer, Experimental Hematology 2011, vol. 39, pp. 2-13.
Hunter et al., Loss of SHIP and CIS Recruitment to the Granulocyte Colony-Stimulating Factor Receptor Contribute to Hyperproliferative Responses in Severe Congenital Neutropenia/Acute Myelogenous Leukemia, The Journal of Immunology, 2004, vol. 173, pp. 5036-5045.
Luo et al., Possible dominant-negative mutation of the SHIP gene in acute myeloid leukemia, Leukemia, 2003 vol. 17, pp. 1-8.
Luo et al., Mutation Analysis of SHIP Gene in Acute Leukemia, Journal of Experimental Hematology, 2004, vol. 12 (4), pp. 420-426.
Metzner et al., Gene transfer of SHIP-1 inhibits proliferation of juvenile myelomonocytic leukemia cells carrying KRAS2 or PTPN11 mutations, Gene Therapy, 2007, vol. 14, pp. 699-703.
Moody et al., Anemia, thrombocytopenia, leukocytosis, extramedullary hematopoiesis, and impaired progenitor function in Pten+/−SHIP−/−mice: a novel model of myelodysplasia, Blood, 2004 vol. 103, No. 12, pp. 4503-4510.
Oki et al., Dok1 and SHIP Act as Negative Regulators of v-Abl-Induced Pre-B Cell Transformation, Proliferation and Ras/Erk Activation, Cell Cycle, vol. 4, No. 2, pp. 310-314.
Ruela-de-Sousa et al., Reversible phosphorylation in haematological malignancies: Potential role for protein tyrosine phosphatases in treatment?, Biochimica et Biophysica Acta, 2010, vol. 1806, pp. 287-303.
Sattler et al., BCR/ABL Directly Inhibits Expression of SHIP, an SH2-Containing Polyinositol-5-Phosphatase Involved in the Regulation of Hematopoiesis, Molecular and Cellular Biology, 1999, vol. 19, No. 11, pp. 7473-7480.
Taylor et al., 59 Phospholipid Phosphatase SHIP-2 Causes Protein Kinase B Inactivation and Cell Cycle Arrest in Glioblastoma Cells, Molecular and Cellular Biology, 2000, pp. 6860-6871.
Viernes et al., Discovery and Development of Small Molecule SHIP Phosphatase Modulators, Medicinal Research Reviews, 2014, vol. 34, No. 4, pp. 795-824.

\* cited by examiner

FIG. 2
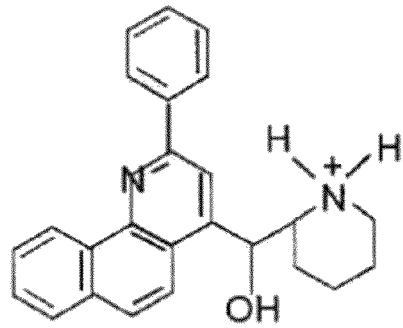
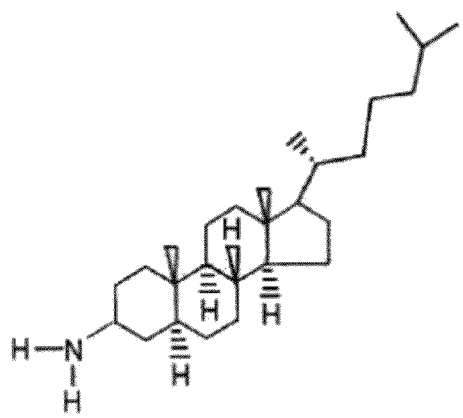
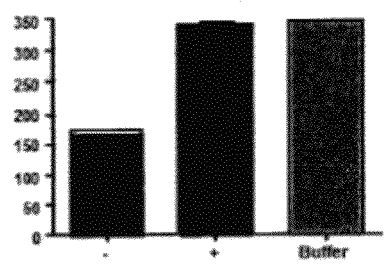
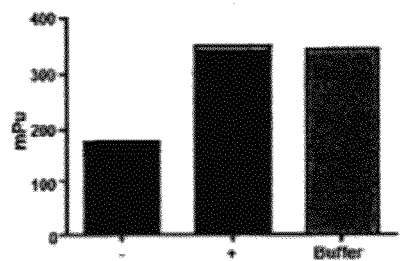
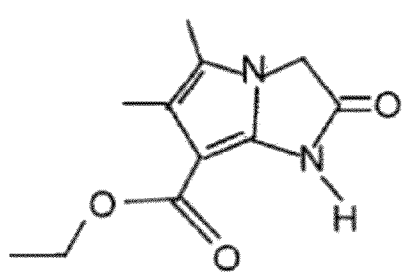
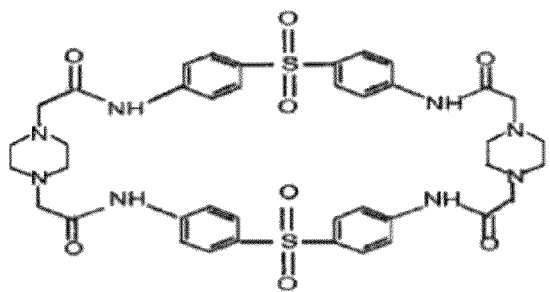
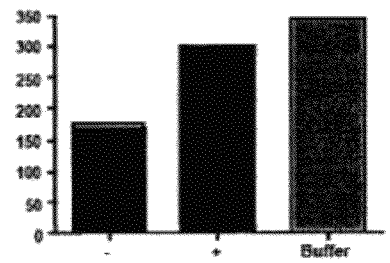
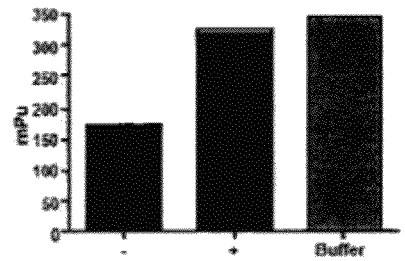

FIG. 4
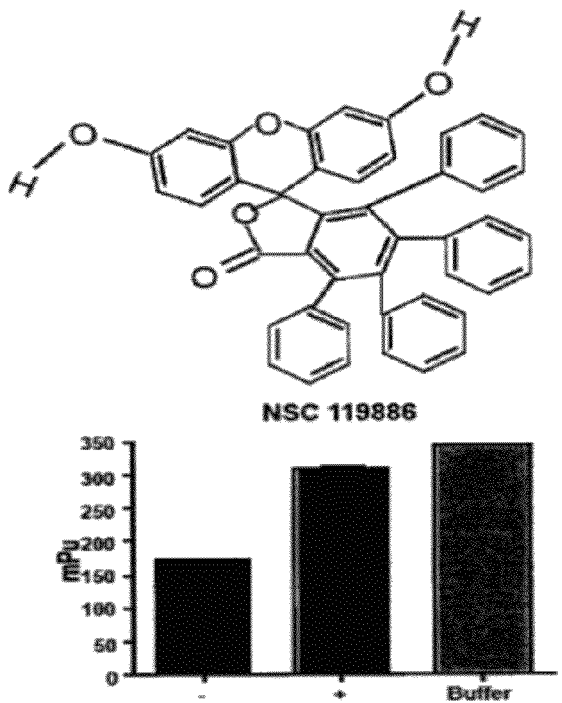
NSC 119886
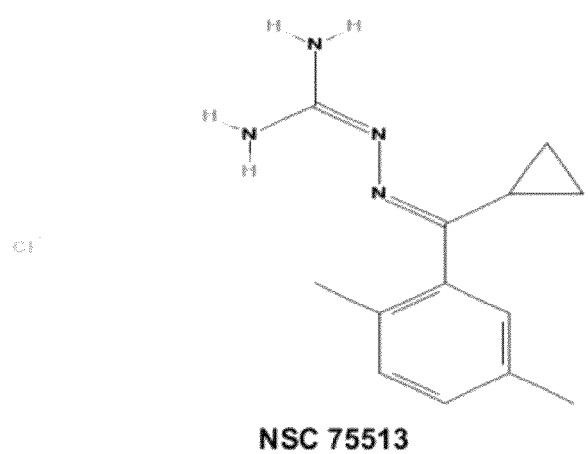
NSC 75513

FIG. 6
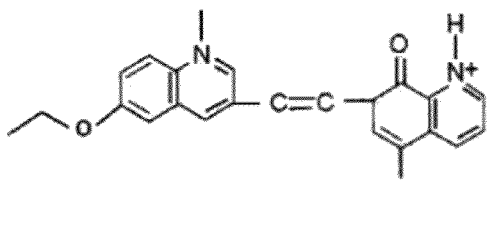
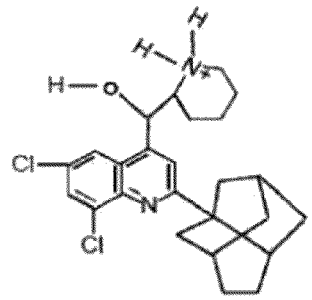
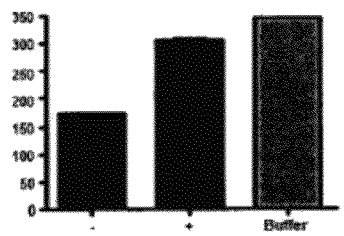
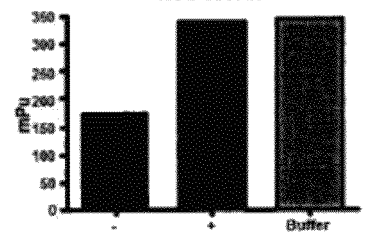
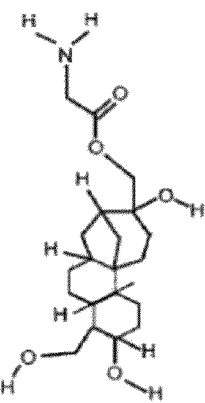
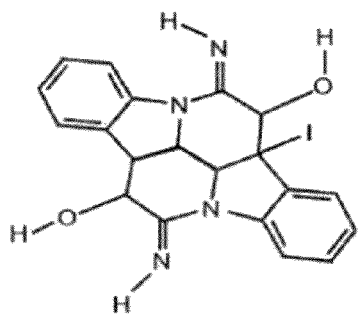
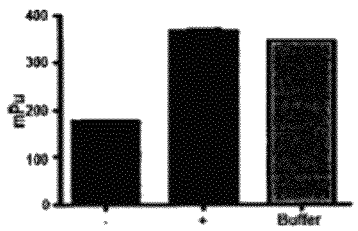
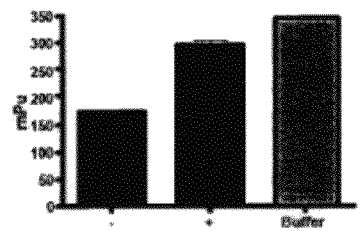

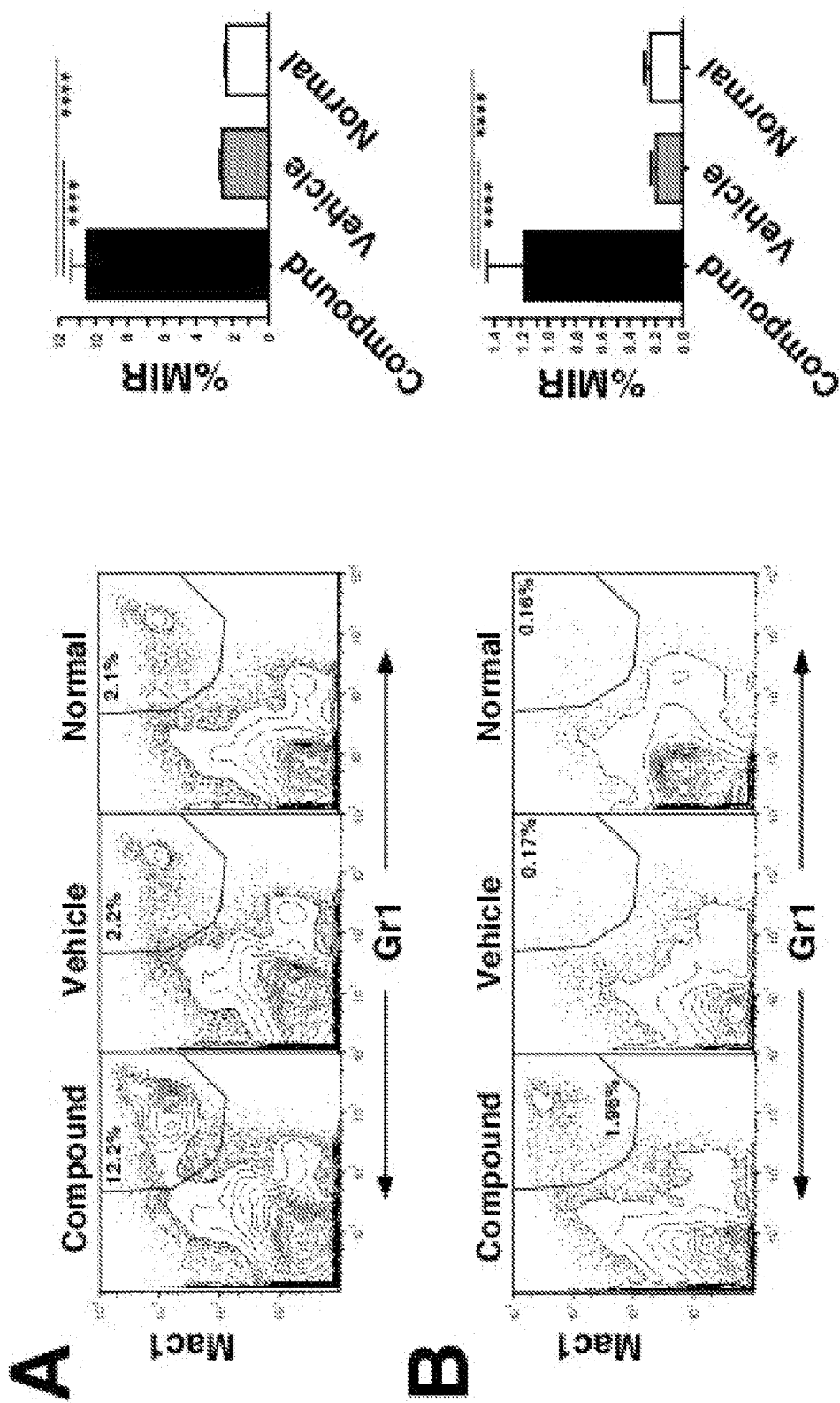
FIG. 16A-B

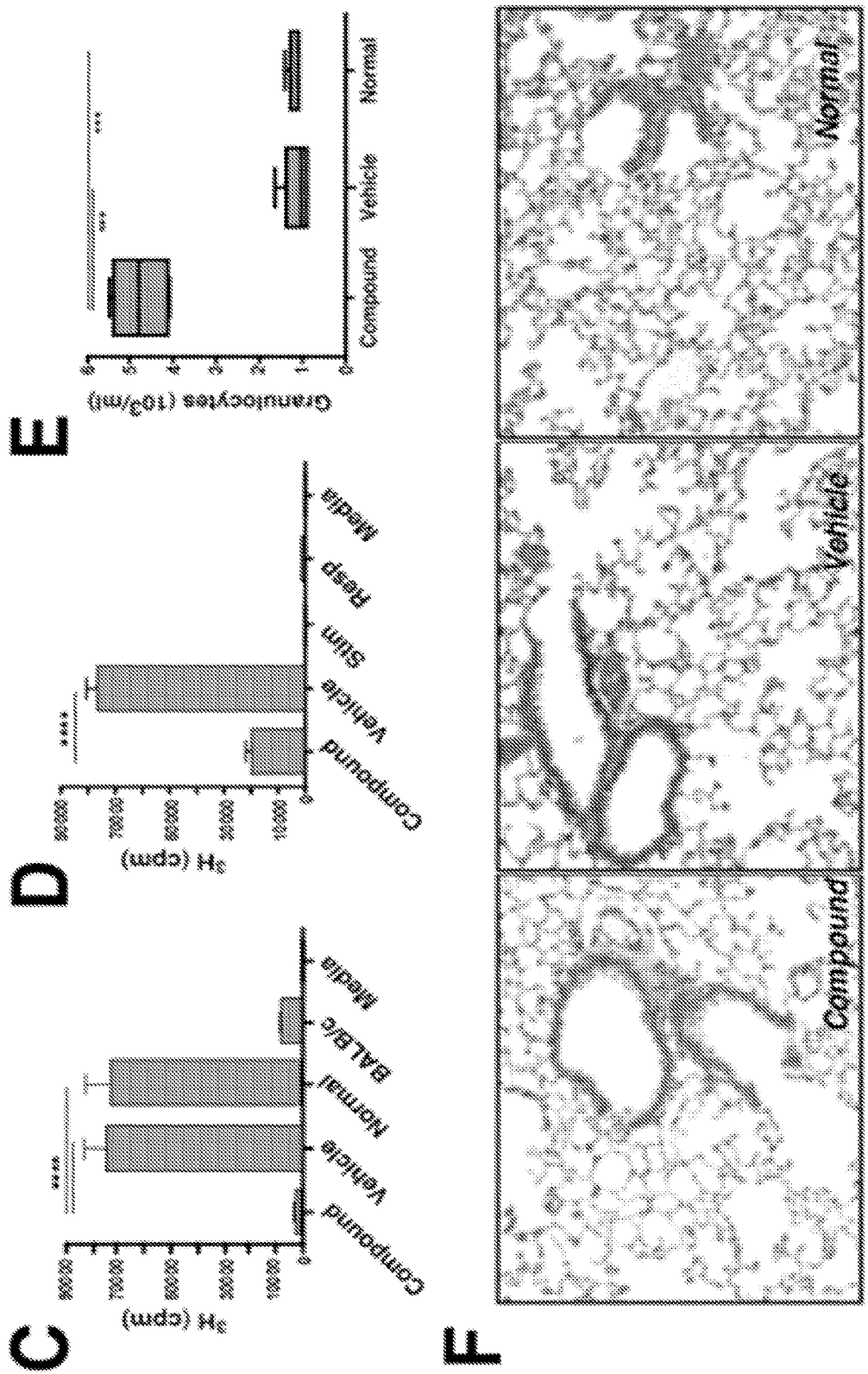
FIG. 16C-F

METHOD OF MODULATING SHIP ACTIVITY

CROSS REFERENCE TO RELATED APPLICATIONS

This application is a continuation of prior filed International Application, Ser. No. PCT/U.S. 2009/060457 filed Oct. 13, 2009, which claims priority to U.S. provisional patent application No. 61/104,883 filed Oct. 13, 2008 which is hereby incorporated by reference into this disclosure

STATEMENT OF GOVERNMENT INTEREST

This invention was made with Government support under grant numbers HL072523 and HL085580 awarded by the National Institutes of Health. The Government has certain rights in the invention.

FIELD OF INVENTION

This invention relates to immune responses. Specifically, the invention includes a method of detecting SHIP activity and compounds useful in modulating an organism's immune response using SHIP.

BACKGROUND OF THE INVENTION

SH2-domain containing inositol phosphatase (SHIP) is a 145 kDa multi-domain cytosolic protein expressed specifically in hematopoietic cells that negatively regulates cell growth, survival and proliferation. SHIP hydrolyzes the phospholipid product phosphoinositol 3,4,5-trisphosphate of PI3K. Specifically, SHIP converts $PI(3,4,5)P_3$ to $PI(3,4)P_2$. This serves to regulate cell survival, proliferation, and differentiation. In this manner, SHIP influences the survival and/or function of numerous cell types, including myeloid cells, osteoclasts, and NK cells.

In genetic models of germline and induced SH2-domain containing inositol 5-phosphatase (SHIP) deficiency, SHIP deficient hosts are permissive for engraftment of major histocompatibility complex (MHC) mismatched bone marrow (BM) grafts, exhibit reduced graft-versus-host disease (GVHD) post-transplant and have delayed rejection of vascularized MHC mismatched heart grafts (unpublished data). In addition, SHIP-deficient mice show an expansion and mobilization of hematopoietic stem cells (HSC) to the blood and spleen. Moreover, recent findings have shown that phosphoinositol phosphatases are important regulators of signaling pathways relevant to both diabetes and cancer.

SUMMARY OF INVENTION

No crystal structure is currently available for SHIP. Consequently, a rational design approach to identify SHIP inhibitors is not feasible. Thus, a high-thoughput screening (HTS) approach was used to identify compounds that can inhibit SHIP's enzymatic activity. A fluorescence polarization assay to detect and quantify SHIP1 activity was developed. This assay was adapted to detect SHIP1 activity and used to screen the Diversity Set from the NCI. This screen yielded 17 hits that have significant inhibitory activity against SHIP1. One of these compounds was found to inhibit the priming of allogeneic T cell response in vitro. In addition, this compound can also induce a significant expansion of MySC and Treg cells in secondary lymphoid tissues of mice. This compound and other SHIP inhibitors described here are useful for the treatment of GvHD and to facilitate engraftment of allogeneic BM and solid organs.

SHIP plays a critical role in cell-mediated allogeneic immune responses. Genetic analysis has revealed that SHIP-deficient hosts are unable to reject BM grafts from multiple different donors with complete MHC mismatches. Moreover, SHIP deficient hosts do not support the priming of allogeneic T cell responses and consistent with this, mice with germline or induced SHIP deficiency exhibit abrogated GvHD following transplant of completely mismatched BM grafts. Thus, SHIP could be targeted to facilitate allogeneic transplantation protocols in the clinic and also to better mobilize HSC for either autologous or allogeneic bone marrow transplant (BMT) protocols. Based on these genetic studies, targeting SHIP in a manner that mimics some of the effects of germline or induced SHIP deficiency offers the opportunity to facilitate allogeneic transplantation. Thus, a fluorescence-based assay was established to measure the enzymatic activity of SHIP and this assay was adapted to a high-throughput screen for chemical inhibitors of SHIP's enzymatic activity. This resulted in the identification of 17 novel SHIP inhibitors, that were shown to also inhibit SHIP2, a potential molecular target in diabetes, but not the 3'-inositol phosphatase PTEN. Two of the more potent SHIP inhibitors, NSC13480 and NSC75513 also inhibit the ability of peripheral lymphoid tissues to prime allogeneic T cell responses in vitro. Consistent with this activity, administration of NSC13480 for a one-week period significantly expands the number of both myeloid and T lymphoid immunoregulatory cells in secondary lymphoid tissues where GvHD is primed. In addition NSC13480 treatment expands the number of NK cells in the periphery of mice and alters their receptor repertoire as has also been observed in $SHIP^{-/-}$ mice. These findings demonstrate the enzymatic activity of SHIP is required for the priming of allogeneic T cells responses and suggest that pharmaceutical modulation of SHIP activity improves the efficacy of allogeneic transplantation therapies.

In a first aspect there is provided a method of treating graft versus host disease in a subject. The includes the step of administering a SHIP1 inhibitor to a subject in need of treatment.

The SHIP1 inhibitor can be a small molecule inhibitor of SHIP1. Advantageously, the SHIP 1 inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP1 inhibitor is 3α-aminocholestane.

In a second aspect there is provided a method of screening a putative SHIP1 inhibitor. The method includes the steps of contacting a SHIP1 protein with a putative SHIP1 inhibitor, contacting the SHIP1 protein with a $PI(3,4,5)P_3$ substrate, and detecting the conversion of $PI(3,4,5)P_3$ to $PI(3,4)P_2$, wherein a reduction in the conversion of $PI(3,4,5)P_3$ to $PI(3,4)P_2$ relative to an uninhibited control indicates that a putative inhibitor inhibits the activity of SHIP1. The putative SHIP1 inhibitor can be a compound from the NCI diversity set. In certain embodiments the SHIP1 protein is an isolated and purified SHIP1 protein. The reaction mixture can include a $MgCl_2$ solution in a concentration of about 20 mM.

In a third aspect there is provided a kit to test the enzymatic activity of SHIP1. The kit can include a recombinant SHIP1 protein, a $PI(3,4,5)P_3$ substrate, and a $PI(3,4)P_2$ detector protein. In certain embodiments the kit can further include a $MgCl_2$ solution in a final concentration of about 20 mM. In certain embodiments the kit can further include a probe to detect bound a PI(3,4)P$_2$ detector protein. The PI(3,4)P2 detector protein probe can be a fluorescent probe.

In a fourth aspect there is provided a method of assaying the enzymatic activity of SHIP1. The method includes the steps of contacting a SHIP1 protein with a PI(3,4,5)P$_3$ substrate and detecting the conversion of PI(3,4,5)P$_3$ to PI(3,4) P$_2$.

In a fifth aspect there is provided a method of inhibiting a SHIP1 protein in a cell. The method includes the step of contacting the cell containing a SHIP1 protein with 3α-aminocholestane.

In a sixth aspect there is provided a method of selectively inhibiting a SHIP1 protein in a cell. The method includes the step of contacting the cell containing a SHIP1 protein with 3α-aminocholestane, wherein the by the 3α-aminocholestane inhibits SHIP1 but does not inhibit SHIP2 or PTEN.

In a seventh aspect there is provided a method for treating or preventing graft-versus-host disease (GVHD) in a recipient of an organ or tissue transplant. The method includes the step of administering to the transplant recipient a SHIP inhibitor in a pharmaceutically effective amount after the transplantation. In certain embodiments the step of administering the SHIP1 inhibitor is performed prior to the organ or tissue transplant. The SHIP1 inhibitor can be a small molecule inhibitor of SHIP1. Advantageously, the SHIP 1 inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP1 inhibitor is 3α-aminocholestane.

In an eighth aspect there is provided a method of modulating SHIP activity in a cell expressing SHIP1 or SHIP2. The method includes the step of contacting the cell with at least one SHIP inhibitor. The SHIP1 inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane. In an advantageous embodiment the SHIP modulation is used to prevent or abrogate at least one disease selected from the group consisting of autoimmune disease, graft-versus-host disease, and solid organ graft rejection, dietary-induced obesity, tumor cell growth. The modulated SHIP can be SHIP1 or SHIP2. In an advantageous embodiment the SHIP modulation is used to prevent or abrogate dietary-induced obesity. In further advantageous embodiments, the SHIP modulation can be used to modulate cell numbers and functions of cells selected from the group consisting of hematopoietic stem cells, NK cells, Treg cells, and myeloid derived suppressor cells. The Treg cells are naïve FoxP3+ T cells. In still further advantageous embodiments, the SHIP modulation is used to convert naïve/effector CD4+ T cells into immunoregulatory cells. In further advantageous embodiments, the SHIP modulation can be used to facilitate engraftment of cells selected from the group consisting of allogenic bone marrow stem cells, hematopoietic stem cells, pluripotent stem cells, IPS, and derivatives thereof.

In a ninth aspect there is provided a method of ex vivo or in vitro treatment of transplants. The method can include the steps of isolating blood derived cells, bone marrow transplants, or organ transplants and contacting the isolated blood derived cells, bone marrow transplants, or organ transplants with a SHIP inhibitor. The treatment of transplants serves to inactivate T-lymphocytes contained in the sample.

In a tenth aspect there is provided a method of inhibiting tumor growth and metastasis in a subject. The method includes the step of administering to the subject one or more SHIP inhibitors. The SHIP1 inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

In a eleventh aspect there is provided a method of treating a hematologic malignancy in a subject. The method includes the step of administering to the subject one or more SHIP inhibitors. The hematologic malignancy can be a leukemia, lymphoma, multiple myeloma, myelodysplastic syndrome (MDS), myeloproliferative disease (MPD) or MDS/MPD diseases. In certain embodiments the leukemia is acute lymphoblastic leukemia, acute myelogenous leukemia, chronic myelogenous leukemia, or chronic lymphocytic leukemia. In certain embodiments the lymphoma is Hodgkin's disease, small lymphocytic lymphoma, diffuse large B-cell lymphoma, follicular lymphoma, mantle cell lymphoma, hairy cell leukemia, marginal zone lymphoma, Burkitt's lymphoma, Post-transplant lymphoproliferative disorder, T-cell prolymphocytic leukemia, B-cell prolymphocytic leukemia, Waldenstrom's macroglobulinemia/lymphoplasmacytic lymphoma, orother NK- or T-cell lymphomas. In certain embodiments the myeloproliferative disease is polycythemia vera, essential thrombocytosis or myelofibrosis. In certain embodiments the MDS/MPD disease is chronic myelomonocytic leukemia, juvenile myelomonocytic leukemia, and atypical chronic myeloid leukemia. The SHIP1 inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

In a twelfth aspect there is provided a method of inducing apoptosis of multiple myeloma cells. The method includes the step of contacting the cells with one or more SHIP inhibitors. The SHIP inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

In a thirteenth aspect there is provided a method of treating multiple myeloma in a subject. The method includes the step of administering to the subject one or more SHIP inhibitors. The SHIP inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

In a fourteenth aspect there is provided a method of inhibiting the proliferation of a human breast cancer cell. The method includes the step of contacting the cell with one or more SHIP inhibitors. The SHIP inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

In a fifteenth aspect there is provided a method of treating breast cancer in a subject. The method includes the step of administering to the subject one or more SHIP inhibitors. The SHIP inhibitor can be a small molecule inhibitor of SHIP1. Advantageously, the SHIP inhibitor can be NSC13480, NSC23922, NSC 624983, NSC 36806, NSC12155, NSC402959, NSC 95609, NSC 143101, NSC 119886, NSC 17383, NSC 86374, NSC 65238, NSC 54340, NSC 86372, NSC 305787, NSC 303812, NSC 118176, or combinations thereof. In a particularly advantageous embodiment the SHIP inhibitor is 3α-aminocholestane.

BRIEF DESCRIPTION OF THE DRAWINGS

For a fuller understanding of the invention, reference should be made to the following detailed description, taken in connection with the accompanying drawings, in which:

FIG. 2 shows the identification of chemical inhibitors of the enzymatic activity of SHIP and FP assays that show SHIP inhibitory activity by the indicated 4 of 17 compounds (i.e. NSC 13480 (IUPAC Name: (2-phenylbenzo[h]quinolin-4-yl)-piperidin-2-ylmethanol. Note: the protonated form is shown in FIG. 2, without a counterion), NSC 23922 ((IUPAC Name: (3R,5S,8R,9S,10S,13R,14S,17R)-10,13-dimethyl-17-[(2R)-6-methylheptan-2-yl]-2,3,4,5,6,7,8,9,11,12,14,15,16,17-tetradecahydro-1H-cyclopenta[a]phenanthren-3-amine), NSC 624983, and NSC 36806) identified during screening of two separate chemical libraries. The black bar graphs indicate reactions in which SHIP was present to generate the PI(3,4)P2 product and thus reduce mP. The presence or absence of each SHIP inhibitor is indicated by + or −. The grey bar graph indicates an assay where buffer was added in lieu of SHIP and thus represents maximal mP reading in the FP assay.

FIG. 4 shows the identification of chemical inhibitors of the enzymatic activity of SHIP and FP assays that show SHIP inhibitory activity by the indicated 1 of 17 (i.e. NSC 119886) compounds identified during screening of two separate chemical libraries. The black bar graphs indicate reactions in which SHIP was present to generate the PI(3,4)P2 product and thus reduce mP. The presence or absence of each SHIP inhibitor is indicated by + or −. The grey bar graph indicates an assay where buffer was added in lieu of SHIP and thus represents maximal mP reading in the FP assay. FIG. 4 also shows the structure of NSC 75513 (IUPAC Name: 2-[(E)-[cyclopropyl-(2,5-dimethylphenyl)methylidene]amino] guanidine chloride).

FIG. 6 shows the identification of chemical inhibitors of the enzymatic activity of SHIP and FP Confirmatory FP assays that show SHIP inhibitory activity by the indicated 4 of 17 compounds identified during screening of two separate chemical libraries. The black bar graphs indicate reactions in which SHIP was present to generate the PI(3,4)P2 product and thus reduce mP. The presence or absence of each SHIP inhibitor is indicated by + or −. The grey bar graph indicates an assay where buffer was added in lieu of SHIP and thus represents maximal mP reading in the FP assay.

FIG. 16 shows that the treatment with SHIP1 inhibitors expands the myeloid immunoregulatory (MIR) compartment and impairs the ability of peripheral lymphoid tissues to prime allogeneic T cell responses. FACS quantitation of Mac1$^+$Gr1$^+$ MIR cells in spleen (A) and lymph node (B) of C57BL/6 mice treated with the SHIP1 inhibitor (Compound), vehicle (Vehicle) or unmanipulated controls (Normal) as indicated. (C) Mixed-Leukocyte-Reactions (MLR) where splenocytes from SHIP1 inhibitor-treated C57BL6 (H2b) mice were used as stimulators for BALB/C (H2d) responders. In parallel splenocytes from either unmanipulated (Normal) or Vehicle treated C57BL6 mice were used as positive controls for the MLR. These results are representative of MLR assays performed with spleen cells from a minimum of three different mice treated with 3α-aminocholestane. (D) Human PBMC were pre-treated for 24 hr with 3α-aminocholestane (Compound) or vehicle, irradiated and then used as stimulators for untreated PBMC from a different donor in a one-way MLR. [BALB/C=responder splenocytes not mixed with BL6 stimulators; Stim=irradiated, SHIP1 inhibitor-treated human PBMC absent responder PBMC; Resp=human PBMC responders absent allogeneic stimulators; Media, media to which only [3H]thymidine was added]. These results are representative of MLR assays performed with three different pairs of human PBMC donors. (E) SHIP1 inhibition increases circulating granulocyte/neutrophil numbers. Mice were treated daily for 7 days with 60 µM SHIP1 inhibitor (Compound), its vehicle (Vehicle) or were unmanipulated (Normal). Absolute peripheral blood granulocyte numbers were determined by an automated blood cell analyzer. (F) SHIP1 inhibition does not cause myeloid-associated lung consolidation and pneumonia. Representative H&E stained lung sections from an 3α-aminocholestane-treated mouse (Compound), a vehicle treated mouse (Vehicle) or an unmanipulated C57BL6 mouse (Normal) as indicated. All images are at 200× magnification.[ *$p<0.05$, $p<0.01$, *$p<0.001$, ****$p<0.0001$]

DETAILED DESCRIPTION OF THE PREFERRED EMBODIMENT

Figure 1:
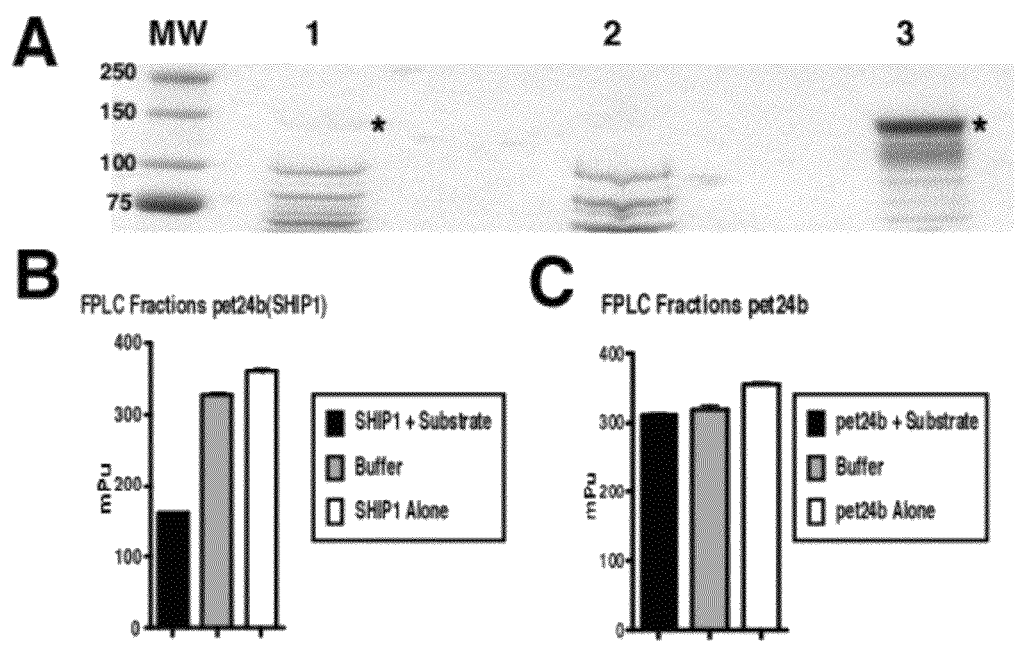
FIG. 1 shows SHIP expression, purification and identification of chemical inhibitors. (A.) Coomassie stained SDS-PAGE gel of *E. coli* lysates that harbor a pet24b(His-SHIP) expression vector (lane 1), FPLC flow through fraction of these lysates (lane 2) and FPLC fractions where the SHIP-His fusion protein elutes from the Ni-resin following an imidazole step gradient (lane 3). The asterisk in lanes 1 and 3 indicates the ~145 kD full-length SHIP protein. (B.) Purified, recombinant SHIP from lane 3 in (A) has significant activity as determined by the reduction in mean polarization units (mPu) in an FP assay designed for 5'-inositol phosphatases (Echelon Biosciences, Salt Lake City, Utah). Note that no significant reduction in mP is obtained when the enzyme buffer without SHIP is added to the FP assay (Buffer) or when purified SHIP is assayed in the absence of its PI(3,4,5)P3 substrate (SHIP only). (C.) FP assay on FPLC fractions which were prepared from *E. coli* that harbor an 'empty' pet24b vector and which show no reduction in mP indicating there is no detectable 5'-inositol phosphatase activity present in comparable FPLC fractions prepared from the same *E. coli* host that does not express SHIP.
Figure 3:
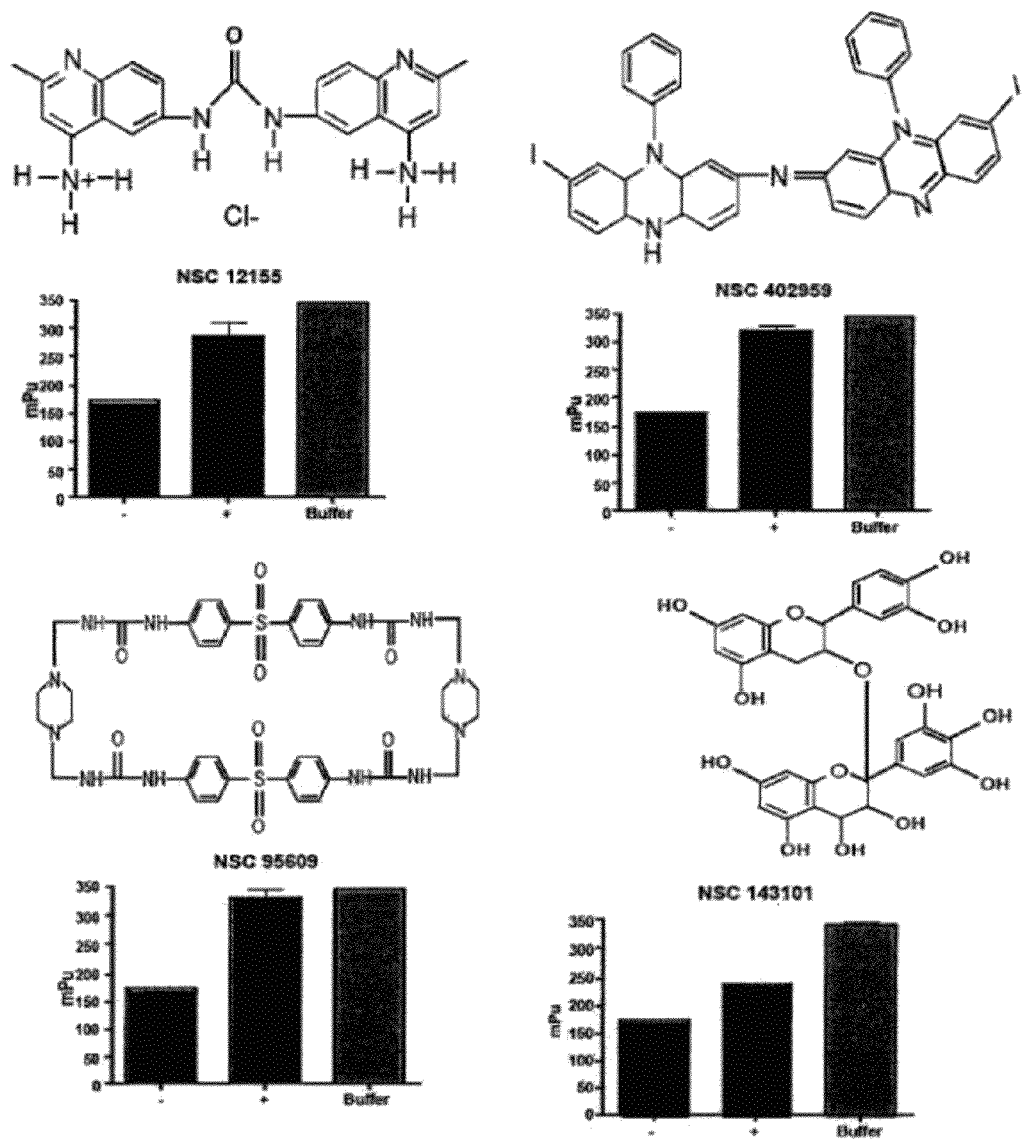
FIG. 3 shows the identification of chemical inhibitors of the enzymatic activity of SHIP and FP assays that show SHIP inhibitory activity by the indicated 4 of 17 compounds identified during screening of two separate chemical libraries. The black bar graphs indicate reactions in which SHIP was present to generate the PI(3,4)P2 product and thus reduce mP. The presence or absence of each SHIP inhibitor is indicated by + or −. The grey bar graph indicates an assay where buffer was added in lieu of SHIP and thus represents maximal mP reading in the FP assay.
Figure 5:
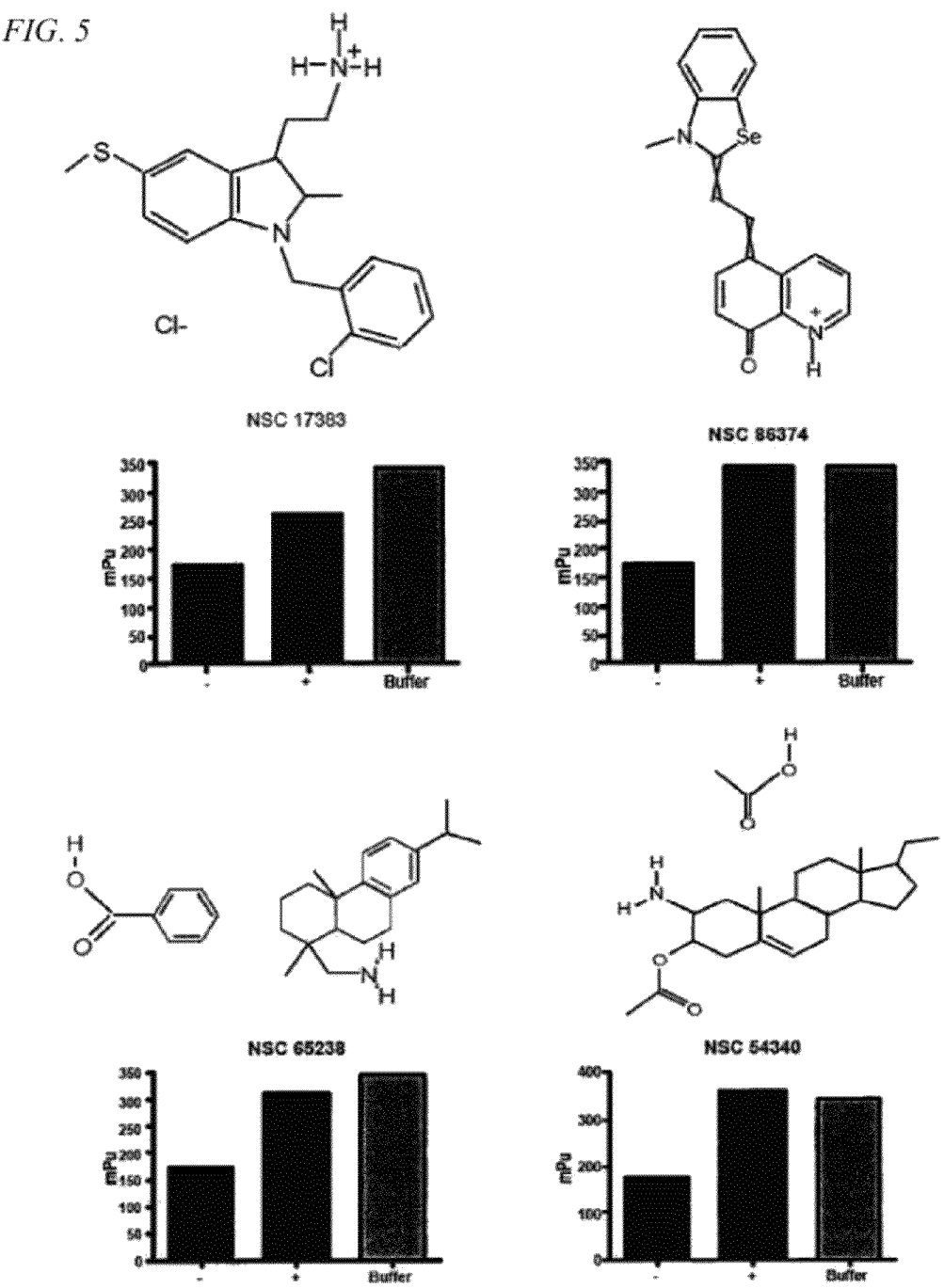
FIG. 5 shows the identification of chemical inhibitors of the enzymatic activity of SHIP and FP Confirmatory FP assays that show SHIP inhibitory activity by the indicated 4 of 17 compounds identified during screening of two separate chemical libraries. The black bar graphs indicate reactions in which SHIP was present to generate the PI(3,4)P2 product and thus reduce mP. The presence or absence of each SHIP inhibitor is indicated by + or −. The grey bar graph indicates an assay where buffer was added in lieu of SHIP and thus represents maximal mP reading in the FP assay.

The present invention provides methods for prevention and clinical treatment of various forms of graft-versus-host disease (GVHD) by using inhibitors of SH2-domain containing inositol phosphatase (SHIP). In particular, novel formulations of SHIP inhibitors are provided for the treatment in order to suppress T-lymphocyte mediated immune responses.

SHIP1-deficiency has been linked to transplant tolerance in genetic studies. Accordingly, molecular targeting of SHIP1 can be utilized to achieve similar effects, including an increase in immunoregulatory capacity. The present invention provides such molecular targeting through the identification of chemical inhibitors of SHIP1, including the molecule 3α-aminocholestane, shown herein to possess important inhibitory properties. Treatment with 3α-aminocholestane significantly expands the myeloid immunoregulatory cell compartment and impairs the ability of peripheral lymphoid tissues to prime allogeneic T cell responses. In addition, 3α-aminocholestane treatment profoundly increases granulocyte production without triggering the myeloid-associated lung consolidation observed in SHIP1$^{-/-}$ mice. Intriguingly, we also find that chemical inhibition of SHIP1 triggers apoptosis of blood cancer cells. Thus, SHIP1 inhibitors represent a novel class of small molecules that have the potential to enhance allogeneic transplantation, boost innate immunity and improve the treatment of hematologic malignancies.

SHIP is critical in cell-mediated allogeneic immune responses, and SHIP deficient hosts do not support priming of allogeneic T cell responses. Targeting SHIP facilitates allogeneic transplantation. Thus, a fluorescence-based assay was established to measure the enzymatic activity of SHIP and adapted to a high-throughput screen for chemical inhibitors of SHIP's enzymatic activity. Seventeen novel SHIP inhibitors were identified that also inhibit SHIP2, a potential molecular target in diabetes, but not PTEN. Two of the more potent SHIP inhibitors, NSC13480 and NSC75513 also inhibit the ability of peripheral lymphoid tissues to prime allogeneic T cell responses in vitro. Administration of NSC13480 expands the number of both myeloid and T lymphoid immunoregulatory cells in secondary lymphoid tissues where GvHD is primed and expands the number of NK cells in the periphery of models. These findings demonstrate the enzymatic activity of SHIP is required for the priming of allogeneic T cells responses.

Seventeen chemical compounds are described and identified herein that can significantly inhibit the enzymatic activity of SHIP in solution. To further validate that compounds identified in the solution based assay for SHIP activity are cell permeable and can alter the immune system in a manner comparable to that observed in SHIP deficient mice, the ability of some of the more potent SHIP inhibitors was tested to inhibit priming of an allogeneic T cell response in vitro and for the ability to expand immunoregulatory cell populations and to abrogate GvHD. A potent inhibitor of SHIP in solution is also shown to inhibit priming of an allogeneic T cell response as measured in an MHC-mismatched MLR and can significantly expand the number of myeloid and T lymphoid immunoregulatory cells in secondary lymphoid tissues.

That SHIP inhibitors identified via a HTS screen can impair priming of allogenic T cells responses in vitro and can expand immunoregulatory cells in lymphoid tissues suggests that chemical inhibition of SHIP activity could be utilized to facilitate allogeneic transplantation procedures. These compounds are useful to enhance engraftment of allogeneic BM as Treg cells are known to not only combat GvHD, but can also facilitate engraftment of donor BM in MHC-mismatched transplant settings. In addition, expansion of myeloid derived suppressor cell (MDSC) and Treg cell numbers also reduces the frequency that donor T cells are primed by host antigen presenting cells (APC) in secondary lymphoid tissues and, thus reduces the incidence and severity of GvHD. As solid organ graft responses by host T cells are also primed in secondary lymphoid tissues, and Treg cells also facilitate solid organ graft acceptance, the SHIP inhibitors identified here will prove useful for reducing organ graft rejection. As SHIP-deficient mice exhibit normal humoral immunity and APC priming of T cell response to foreign antigens, the compounds described here spare normal adaptive immune function. Thus, they offer a more selective method to dampen deleterious host and donor allogenic T cell responses without compromising adaptive immune functions necessary to combat opportunistic pathogens that frequently infect transplant patients undergoing conventional immunosuppressive therapies.

Figure 13:
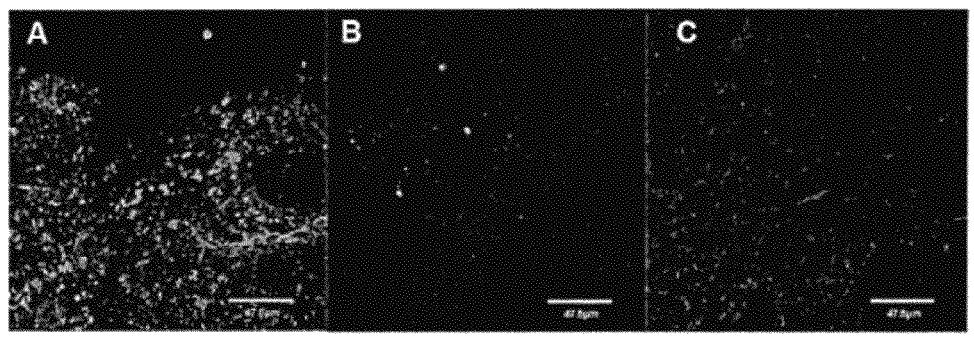
FIG. 13 shows SDF1/CXCL12 expression is profoundly diminished in the bone marrow of SHIP$^{-/-}$ mice. Representative photomicrographs at 63× for frozen sections were prepared from the femur of adult (A) SHIP$^{+/+}$ and (B) SHIP$^{-/-}$ mice that were stained with biotinylated anti-SDF1 Ab (MAB350, R&D Systems) (A, B) or a biotinylated IgG1κ control antibody (C) (MOPC-31C, Becton Dickinson). Staining by the anti-SDF1 Ab or the IgG1κ control Ab was revealed by a secondary stain consisting of SA-AlexaFluor 546 (Molecular Probes). The background SDF1 staining observed with SHIP$^{-/-}$ BM sections were consistently comparable to staining observed in isotype control stains performed on both SHIP$^{-/-}$ and WT femurs (C and data not shown).
Figure 14:
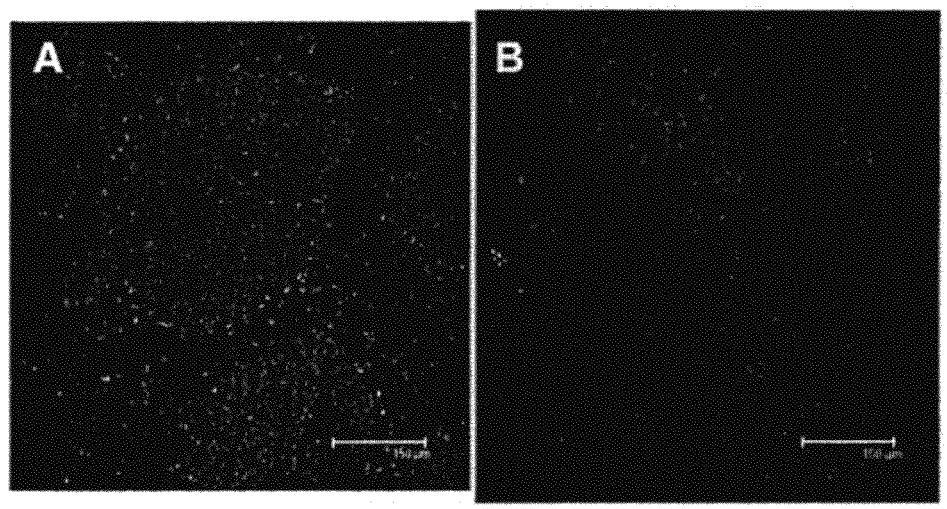
FIG. 14 shows SDF1/CXCL12 expression is profoundly diminished in the spleen of SHIP$^{-/-}$ mice. Representative photomicrographs at 63× of frozen sections prepared from the spleens of adult (A) SHIP$^{+/+}$ and (B) SHIP$^{-/-}$ mice that were stained with biotinylated anti-SDF1 Ab (MAB350, R&D Systems) or a biotinylated IgG1κ control antibody (MOPC-31C, Becton Dickinson). Staining by the anti-SDF1 Ab or the IgG1κ control Ab was revealed by a secondary stain consisting of SA-AlexaFluor 546 (Molecular Probes, bright dots). The light grey stains specific for IgD and reveals B lymphocyte areas in the spleen.

SHIP inhibition also prevents chemo-attraction of tumor cells to directed tissues in vivo. SDF1 serves as a chemo-attractant to lure stem cells and tumor cells into tissue sites, referred to as metastasis for tumor cells. There is very little or no SDF1/CXCL12 produced in BM [bone marrow] or solid organs (e.g. spleen) in SHIP-deficient mice, seen in FIGS. 13 and 14. Thus SHIP inhibitors may be administered to shut down or significantly reduce production of SDF1/CXCL12 in tissues and organs. The SHIP inhibitors are also useful to inhibit tumor growth and metastasis in solid organs and tissues.

The present disclosure further describes the identification and initial in vivo characterization of a small molecule inhibitor of the SHIP1 enzyme. To validate that this compound, identified in a solution based assay for SHIP1 activity, is cell permeable and can alter the immune system in a manner comparable to that observed in SHIP1 deficient mice, its ability to expand MIR cells and to consequently inhibit priming of an allogeneic T cell response was tested. It is shown herein that chemical inhibition of SHIP1 is capable of both. In addition, SHIP1 inhibition promotes a profound increase in circulating granulocyte numbers and apoptosis of blood cancer cells.

It is also shown that administration of a SHIP1 inhibitor can expand immunoregulatory cells in peripheral lymphoid tissues and suppress priming of allogeneic T cell responses. Because allogeneic T cell responses that culminate in GvHD or solid organ graft rejection are primed in peripheral lymphoid tissues, [Lafferty K J, et al., Surg Clin North Am (1986) 66(6):1231-1253; Kosaka H, et al., J Exp Med (1992) 176(5): 1291-1302; Shlomchik W D, et al., Science (1999) 285 (5426):412-415] these results show that 3α-aminocholestane (NCS23922), and potentially other SHIP1 selective inhibitors, might be used to limit deleterious T cell responses that mediate GvHD and organ graft rejection. Consistent with this, GvHD is reduced and cardiac graft rejection delayed in adult mice rendered SHIP1-deficient [Paraiso K H, et al., *J Immunol* (2007) 178(5):2893-2900; Collazo M M, et al., *Blood* (2009) 113:2934-2944]. As SHIP1-deficient mice exhibit normal humoral immunity [Brauweiler A, et al., *J Exp Med* (2000) 191(9):1545-1554; Liu Q, et al., J Exp Med (1998) 188(7):1333-1342] and priming of T cell responses to naive antigens [Ghansah T, et al., *J Immunol* (2004) 173(12): 7324-7330], the SHIP1 inhibitor described here, and potentially others, may not significantly compromise adaptive immune function. Thus, 3α-aminocholestane offers a more selective method to dampen deleterious host and donor allogeneic T cell responses without compromising adaptive immune functions necessary to combat opportunistic pathogens that can compromise the recovery and survival of transplant patients receiving state-of-the-art immunosuppressive regimens.

Increased Akt signaling and survival in primary NK [Wang J W, et al., *Science* (2002) 295(5562):2094-2097] and myeloid cells [Liu Q, et al., Genes & Development (1999) 13(7):786-791] isolated from SHIP1$^{-/-}$ mice have been documented. However, there is also an emerging role for the SHIP1/2 product PI(3,4)P2 in promoting Akt activation [Franke T F, et al., *Science* (1997) 275(5300):665-668] and tumorigenicity. [Ivetac I, et al., *EMBO Rep* (2009) 10(5):487-493] Thus, via generation of PI(3,4)P2, SHIP1/2 could amplify survival signals in transformed or neoplastic cells by providing additional plasma membrane locations for recruitment and activation of PH-domain containing kinases, such as Akt. Indeed, PI(3,4)P2 levels are found to be increased in leukemia cells. [Jain S K, et al., *Blood* (1996) 88(5):1542-1550] Consistent with this hypothesis, it is shown that a SHIP1 selective inhibitor reduces Akt activation and promotes apoptosis of human blood cell cancers that express SHIP1. Thus, SHIP1 inhibition can be used as an adjunct to other therapeutics to further decrease the survival of hematologic malignancies. There will also be applications for SHIP1/2 inhibitors in non-hematologic cancers as SHIP2 expression is increased in breast cancer and promotes survival signals from EGF-R in these cells. [Prasad N K, et al., *Tumour Biol* (2008) 29(5):330-341; Prasad N K, et al., *Carcinogenesis* (2008) 29(1):25-34; Prasad N K, *Int J Oncol* (2009) 34(1):97-105]

Although treatment of mice with a SHIP1 selective inhibitor induced many of the same myeloid phenotypes observed in mice that are genetically SHIP1-deficient, some key deleterious effects associated with genetic SHIP1 deficiencies were notably absent. Importantly, we did not to observe myeloid lung consolidation and pneumonia emerging in inhibitor-treated mice. This could be fortuitous, since this pneumonia is the major pathology that limits the lifespan of SHIP1$^{-/-}$ mice.[Helgason C D, et al. (1998) Genes & Development 12(11):1610-1620] Without wishing to be bound to a particular theory, there are several reasons that chemical inhibition of SHIP1 enzymatic activity and germline SHIP1 deficiency do not result in identical hematologic manifestations. In germline SHIP1-deficient mice there is complete loss of SHIP1 protein from the point of conception and, thus, the developmental effects of SHIP 1-deficiency may trigger some abnormalities that may not occur in the treatment of adult mice with a SHIP1 inhibitor. Although it has been documented that several SHIP1 phenotypes are induced in MxCreSHIP1$^{flox/flox}$ mice rendered SHIP1-deficient as adults, [Ghansah T, et al., J Immunol (2004) 173(12):7324-7330; Hazen A L, et al., Blood (2009) 113(13):2924-2933; Collazo M M, et al., Blood (2009) 113:2934-2944] these mice have not been examined for lung pathology. Another possible explanation for the difference between chemical and genetic ablation of SHIP1 function is that a SHIP1 null mutation results in the absence of SHIP1 protein. The absence of SHIP1 protein has the potential to permit inappropriate activities by other signaling proteins that assume its place in cell signaling complexes. In fact, this is known to occur in SHIP1$^{-/-}$ NK cells, as loss of SHIP1 expression leads to inappropriate recruitment of SHPT to the 2B4 SLAM family receptor converting this receptor from activating mode to a dominant inhibitory mode. [Wahle J A, et al., J Immunol (2007) 179(12):8009-8015] It is possible then that the myeloid lung consolidation observed in SHIP1$^{-/-}$ mice also results from inappropriate activity by another signaling protein that fills the void left by the absence of SHIP1 protein. Further analysis of these questions could provide mechanistic insights into the role that SHIP1 plays in alveolar macrophage biology.

In addition to the above effects relevant to allogeneic transplantation, SHIP1 inhibitors will also offer benefits to cancer patients. For instance, a SHIP1 inhibitor could be used to enhance granulocyte recovery after autologous BMT or high dose chemo/radiotherapy that frequently compromises granulocyte production and function. Granulocytes serve as the first line of defense against bacterial, fungal and parasitic infections and thus play a prominent role in recovery following myeloablative therapies. In addition, the growth and survival of SHIP1-expressing blood cell malignancies is significantly reduced by chemical inhibition of SHIP1. Thus, SHIP1 inhibitors represent a novel class of compounds that could potentially find utility in both transplantation and the treatment of cancer.

Treatment of GVHD

In one embodiment, a method is provided for treating a patient suffering from GVHD. The method comprises administering to the GVHD patient a composition including an SHIP inhibitor.

Dosage amounts and frequency will vary according to the particular SHIP inhibitor, the dosage form, and individual patient characteristics. Generally speaking, determining the dosage amount and frequency for a particular SHIP inhibitor (e.g., 3α-aminocholestane), dosage form, and individual patient characteristic can be accomplished using conventional dosing studies, coupled with appropriate diagnostics.

In a particular embodiment, a SHIP inhibitor such as 3α-aminocholestane is used to treat patients that have acute Graft vs Host Disease (aGVHD) but failed at least one immunosuppressive regimen such as a regimen including steroids such as prednisone and methylprednisolone, cyclophosphamide, cyclosporin A, FK506, thalidomide, azathioprine, and daclizumab. For example, hematopoietic stem cell transplant (HSCT) patients manifesting grade 2 or greater aGVHD, who have failed to respond to treatment with at least 2 mg/Kg of methylprednisolone or equivalent corticosteroid or other salvage therapy, can be treated with a SHIP1 inhibitor.

GVHD Prophylaxis

A SHIP inhibitor such as 3α-aminocholestane can also be used as a prophylaxis to prevent onset of GVHD or to reduce the effects of GVHD.

A SHIP inhibitor such as 3α-aminocholestane may be administered as a GVHD prophylaxis to a transplant recipient within a predetermined time window before or after the transplantation.

In one embodiment, a SHIP inhibitor such as 3α-aminocholestane may be administered to the recipient on days −3 or −2 (i.e., 3 or 2 days before the transplantation) as part of a non-myeloablative conditioning regimen, then followed by transplantation such as hematopoietic stem cell infusion. Alternatively, a SHIP inhibitor such as 3α-aminocholestane may be administered as a GVHD prophylaxis to a transplant recipient after the transplantation. For example, for standard (i.e., myeloablative) transplant or non-myeloablative stem cell transplant (NST) where 3α-aminocholestane is not used in the conditioning regimen, 3α-aminocholestane is administered to the transplant recipient at 0.5-1.5 mg/m$^2$/day on days +8, +15, +22 and +30 following stem cell infusion.

Combination Therapy for GVHD

Besides use in a single-agent treatment or prevention of GVHD, the SHIP inhibitor such as 3α-aminocholestane can also be used in a combination therapy for acute or chronic GVHD. The combination therapy may have synergistic therapeutic effects on the patients and thus requires lower amount of 3α-aminocholestane and the other agent used in conjunction to achieve satisfactory therapeutic efficacy. As a result, potential side effects associated with high dose of drugs, such as myelosuppression, are reduced and the patient's quality of life is improved.

Various other therapeutic agents may be combined with the SHIP inhibitor for the treatment or prevention of GVHD. The other therapeutic agents include, but are not limited to, immunosuppressive agents such as steroids (e.g., prednisone and methylprednisolone), cyclophosphamide, cyclosporin A, FK506, thalidomide, azathioprine, monoclonal antibodies (e.g., Daclizumab (anti-interleukin (IL)-2), Infliximab (anti-tumor necrosis factor), MEDI-205 (anti-CD2), abx-cbl (anti-CD147)), and polyclonal antibodies (e.g., ATG (anti-thymocyte globulin)). For example, 3α-aminocholestane may be combined with a steroid such as methylprednisolone to treat aGVHD. However, such a combination may be too broadly immunosuppressive to render the patient more susceptible to opportunistic infection.

For the treatment of acute GVHD, a SHIP inhibitor such as 3α-aminocholestane may preferably be combined with monoclonal antibodies which specifically target T-cells such as Infliximab, Daclizumab, MEDI-205, or abx-cbl. The monoclonal antibody may be administered at the FDA-approved dosage and by its standard route of administration (e.g., IV), followed by oral or parenteral administration of 3α-aminocholestane.

The SHIP inhibitor may also be used in conjunction with other immunosuppressive agents as prophylaxis for GVHD post-transplantation. For example, the recipient of bone marrow transplant may be treated with 3α-aminocholestane in conjunction with a standard post infusion regimen including mini-methotrexate at 5 mg/m$^2$ (as opposed to the conventional dose at 10-15 mg/m$^2$), cyclosporine A (5-6 mg/Kg/d IV or 10-18 mg/Kg/d orally) and FK506 (0.05-0.1 mg/Kg/d IV or 0.15-0.3 mg/Kg/d orally).

In addition, 3α-aminocholestane may be used in conjunction with other types of therapy as prophylaxis for GVHD prior to transplantation. For example, the recipient of bone marrow transplant may be pretreated with 3α-aminocholestane in conjunction with TBI (radiation), phototherapy, melphalan, cyclophosphamide or ATG to prevent the onset of GVHD.

Ex Vivo Treatment of Transplants Using SHIP Inhibitors

In yet another aspect, the invention relates to a method of ex vivo or in vitro treatment of blood derived cells, bone marrow transplants, or other organ transplants. The method comprises treating the blood derived cells, bone marrow transplants, or other organ transplants with an SHIP inhibitor (e.g., 3α-aminocholestane) in an effective amount such that activities of T-lymphocytes therein are substantially inhibited, preferably by at least 50% reduction in activity, more preferably by at least 80% reduction in activity, and most preferably by at least 90% reduction in activity.

The invention is practiced in an in vitro or ex vivo environment. All of the discussion above regarding clinical treatment or prevention of GVHD that is relevant to an in vitro or ex vivo environment applies to this practice. In a particular embodiment, practice of an in vitro or ex vivo embodiment of the invention might be useful in the practice of immune system transplants, such as bone marrow transplants or peripheral stem cell procurement. In such procedures, the SHIP inhibitor might be used, as generally described above, to treat the transplant material to inactivate T-lymphocytes therein so that the T-lymphocyte mediated immune response is suppressed upon transplantation.

For example, the SHIP inhibitor may be added to a preservation solution for an organ transplant in an amount sufficient to inhibit activity of T-lymphocytes of the organ. Such a preservation solution may be suitable for preservation of different kind of organs such as heart, kidney and liver as well as tissue therefrom. An example of commercially available preservation solutions is Plegisol (Abbott), and other preservation solutions named in respect of its origins include the UW-solution (University of Wisconsin), the Stanford solution and the Modified Collins solution. The preservation solution may also contain conventional co-solvents, excipients, stabilizing agents and/or buffering agents.

The dosage form of the SHIP inhibitor may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

The preservation solution or buffer containing an SHIP inhibitor (e.g., 3α-aminocholestane) may also be used to wash or rinse an organ transplant prior to transplantation or storage. For example, a preservation solution containing pentostatin may be used to flush perfuse an isolated heart which is then stored at 4°.

In another embodiment, practice of the invention might be used to condition organ transplants prior to transplantation. Prior to transplantation a SHIP inhibitor such as 3α-aminocholestane may be added to the washing buffer to rid the transplant of active T-lymphocytes. In this way, the risk of developing acute GVHD upon transplantation should be significantly reduced, and the host is not only protected from GVHD but also from potential side effects of the SHIP inhibitor. The concentration of the SHIP inhibitor in the preservation solution or wash buffer may vary according to the type of transplant. Other applications in vitro or ex vivo using an SHIP inhibitor will occur to one of skill in the art and are therefore contemplated as being within the scope of the invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment.

Kits for practicing the methods of the invention are further provided. By "kit" is intended any manufacture (e.g., a package or a container) comprising at least one reagent, e.g., an antibody, a nucleic acid probe, etc. for specifically detecting the expression of a biomarker of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

A "subject in need of treatment" is a mammal with a condition that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The following examples are provided for the purpose of illustration and are not intended to limit the scope of the present invention.

Example 1

Expression, Purification and Measurement of Recombinant SHIP Activity

An E. coli based system was developed for expression of recombinant SHIP, as shown in FIG. 1a, to allow the efficient screening of chemical libraries for compounds that inhibit SHIP's enzymatic activity. SHIP is detectable in this expression system as a ~145 kD protein (FIG. 1a, lane 1). Because of an in-frame Histidine (His) tag on the COOH terminus of SHIP, it can then be purified from E. coli lysates by FPLC over a Ni-containing resin. (FIG. 1a, lane 3). Purified SHIP was routinely obtained in sufficient quantities, using this E. coli expression system and FPLC purification, to conduct high-throughput screening (HTS) of chemical libraries for compounds that inhibit SHIP activity. However, prior to screening, a fluorescence polarization (FP) assay that detects SHIP activity in either a 96- or 386-well format, seen in FIG. 1b, screen was established. SHIP generates $PI(3,4)P_2$ from its $PI(3,4,5)P_3$ substrate. In the FP assay enzymatic generation of $PI(3,4)P_2$ by SHIP reduces polarized fluorescence (mP) because the fluorescent $PI(3,4)P_2$ "probe" is displaced from a detector protein that binds specifically to PI(3,4)P2. The FP assay is highly specific for SHIP activity in these lysates. No significant 5'-inositol phosphatase activity was detected in E. coli lysates harboring an 'empty' pet24b expression vector insert when FPLC fractions where SHIP typically elutes with the imidazole step gradient are analyzed in the FP assay (FIG. 1c).

Example 2

Identification of SHIP Inhibitors by HTS

After preparing purified SHIP and establishing the FP assay, two different chemical libraries, comprising a total of ~2100 different chemical compounds, were screened. Seventeen compounds capable of inhibiting SHIP activity at µM concentrations were identified in this screen. The compounds were verified for SHIP activity inhibition by repeating the FP assay with the compounds obtained from their respective wells in the replicates of the masterplates for these libraries FIGS. 2-6).

Example 3

SHIP1 Inhibitors Exhibit Selectivity for 5' Inositol Phopshatases

Figure 7:
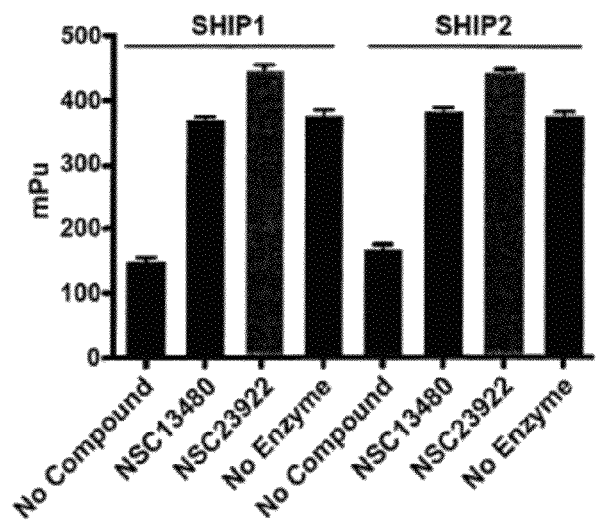
FIG. 7 shows SHIP1 inhibitors can also exhibit comparable inhibitory activity against the other SHIP enzyme expressed by mammalian cells, SHIP2. NSC13480 and NSC23922 inhibit both SHIP1 and SHIP2 enzymatic activity as measured in the FP assay described above. No Compound—FP assay conducted with purified SHIP1 or SHIP2 as indicated in the absence of inhibitor. No Enzyme—FP assay conducted in SHIP buffer and fluorescent substrate in the absence of enzyme.
Figure 8:
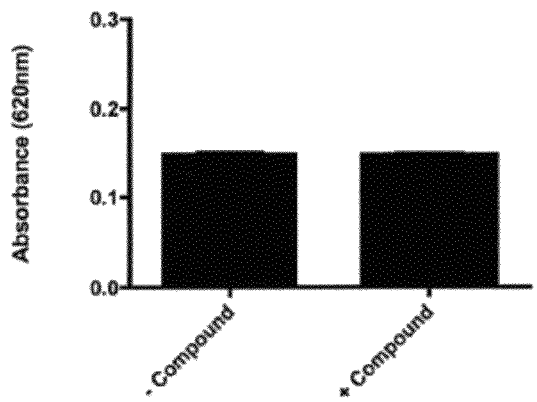
FIG. 8 shows SHIP inhibitor NSC13480 exhibits no significant inhibition of nPTEN at 100 μM (+ Compound) as compared to a PI(3,4,5)P$_3$ hydrolysis reaction where no NSC 13480 was added (− Compound). The absorbance measurements shown correspond to liberated PO$_4$ generated by recombinant PTEN (1.44 μg) when incubated with its substrate, PI (3,4,5)P$_3$, as detected by a Malachite Green reporter.

To determine whether the SHIP1 inhibitor described above exhibits selectivity for SHIP1, the other two known inositol phosphatases in the mammalian cell that, like SHIP1, can modulate or oppose PI3K, SHIP2 and PTEN were assessed. FIG. 8 shows that NSC13480 does not inhibit PTEN. Conversely, FIG. 7 shows that both NSC13480 and NSC23922 inhibit SHIP1 and SHIP2, seen in FIG. 7. Thus far, none of the inhibitors have been identified as selective for SHIP1 over SHIP2. The majority of SHIP inhibitors identified show selectivity for 5' inositol phosphatases and thus might be used to target SHIP1 or SHIP2 activity.

3'-phosphoinositol phosphatase, phosphatase homologous to tensin (PTEN), is both a tumor suppressor and a negative regulator of insulin action (Prasad, N. K., et al., Phosphoinositol phosphatase SHIP2 promotes cancer development and metastasis coupled with alterations in EGF receptor turnover, *Carcinogenesis.* 2008 Jan;29(1):25-34.). 5'-phosphoinositol phosphatase, SH2-containing 5'-inositol phosphatase 2 (SHIP2), regulates insulin signaling and its genetic knockout prevents high-fat diet-induced obesity in mice. SHIP2 also regulates cytoskeleton remodeling and receptor endocytosis. These results, combined with the fact that both PTEN and SHIP2 act on the same substrate, implicate a potential role for SHIP2 in cancer. The results shown herein indicate that, in direct contrast to PTEN, SHIP2 protein expression is elevated in a number of breast cancer cell lines. RNA interference-mediated silencing of SHIP2 in MDA-231 cells suppresses epidermal growth factor receptor (EGFR) levels by means of enhanced receptor degradation. Furthermore, endogenous SHIP2 in MDA-231 breast cancer cells supports in vitro cell proliferation, increases cellular sensitivity to drugs targeting the EGFR and supports cancer development and metastasis in nude mice. In addition, significantly high proportions (44%; P=0.0001) of clinical specimens of breast cancer tissues in comparison with non-cancerous breast tissues contain elevated expression of SHIP2 protein. Taken together, these results demonstrate that SHIP2 is a clinically relevant novel anticancer target that links perturbed metabolism to cancer development.

Genetic ablation of Inpp11, which encodes SHIP2 (SH2-domain containing inositol 5-phosphatase 2), was reported to induce severe insulin sensitivity, leading to early postnatal death. In the study, the targeting construct left the first eighteen exons encoding Inpp11 intact, generating an Inpp11 (EX19-28–/–) mouse, and apparently also deleted a second gene, Phox2a.

A novel SHIP2 knockout (Inpp11 (–/–)) targeted to the translation-initiating ATG, which is null for Inpp11 mRNA and protein is examined herein. Inpp11(–/–) mice are viable, have normal glucose and insulin levels, and normal insulin and glucose tolerances. The Inpp11 (–/–) mice are, however, highly resistant to weight gain when placed on a high-fat diet. These results indicate that inhibition of SHIP2 is useful in the effort to ameliorate diet-induced obesity, but call into question a dominant role of SHIP2 in modulating glucose homeostasis.

Example 3

Figure 9:
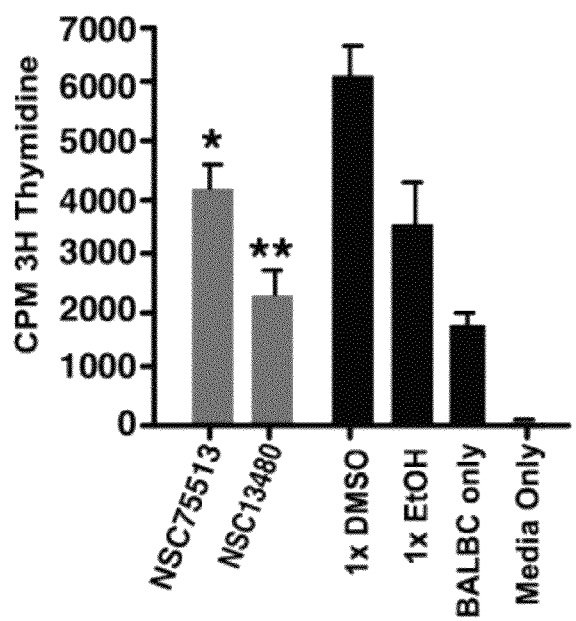
FIG. 9 shows the identification of SHIP inhibitors from HTS that reduce priming of allogeneic T cell responses in vitro. Mean proliferation of 100K BALB/C responders as measured by $^3$H-Thymidine uptake after exposure to 200K irradiated BL6 stimulators that were treated with the indicated compound, 1×DMSO or 1× EtOH prior to initiation of the mixed leukocyte reaction (MLR). 1×DMSO serves as the allogeneic MLR positive control for all compounds with the exception of HLM85321 for which 1× EtOH is the positive control. [*p<0.05, **p<0.01].

Treatment of Cells from Secondary Lymphoid Tissues with SHIP Inhibitors Decreases their Ability to Prime Allogeneic T Cells Responses Spleen cells and lymphe node LN cells are normally robust stimulators of allogeneic T cell responses in the one-way mixed leukocyte reaction (MLR) assay, but they are very poor stimulators when obtained from mice with germline or induced SHIP-deficiency. The MLR assay provides a rapid in vitro test to determine if a putative SHIP inhibitor is cell permeable, can act on primary hematolymphoid cells, and can modulate some of the same immune functions found in altered in SHIP$^{-/-}$ mice. The ability of two of the more potent SHIP inhibitors, NSC13480 and NSC75513 (identified in the above HTS screen), were tested for their ability to significantly inhibit MHC-mismatched spleen cells for the priming of allogeneic T cell responses in vitro. The results of these tests are shown in FIG. 9. Murine splenocytes were cultured with NSC13480 and NSC75513 for 72 hr. The compound was added at 0, 24 and 48 hr to the cultures. Consistent with studies of SHIP-deficient splenocytes from both germline and MxCreSHIP$^{flox/flox}$ mice, NSC13480 and NSC75513 significantly inhibited the ability of C57B16/J splenocytes to prime allogeneic T cell responses by BALB/C responders in the one-way MLR assay (FIG. 8). Moreover, the degree of BALB/C proliferation that was observed in the allogeneic MLR primed by splenocytes treated with NSC13480 was not significantly greater than that observed with BALB/C splenocytes cultured in the absence of BL6 stimulators, indicating there was no appreciable allogeneic T cell response after treatment of stimulator cells with NSC13480. Splenocytes treated with NSC13480 have consistently shown a complete inability to prime allogeneic T cell responses in multiple MLR assays. Taken together with the findings presented in FIGS. 2-6, discussed above, these results indicate that a chemical inhibitor of SHIP's enzymatic activity in solution is also cell permeable and can antagonize the priming of allogeneic T cell responses by cells from secondary lymphoid organs.

Example 4

Figure 10A:
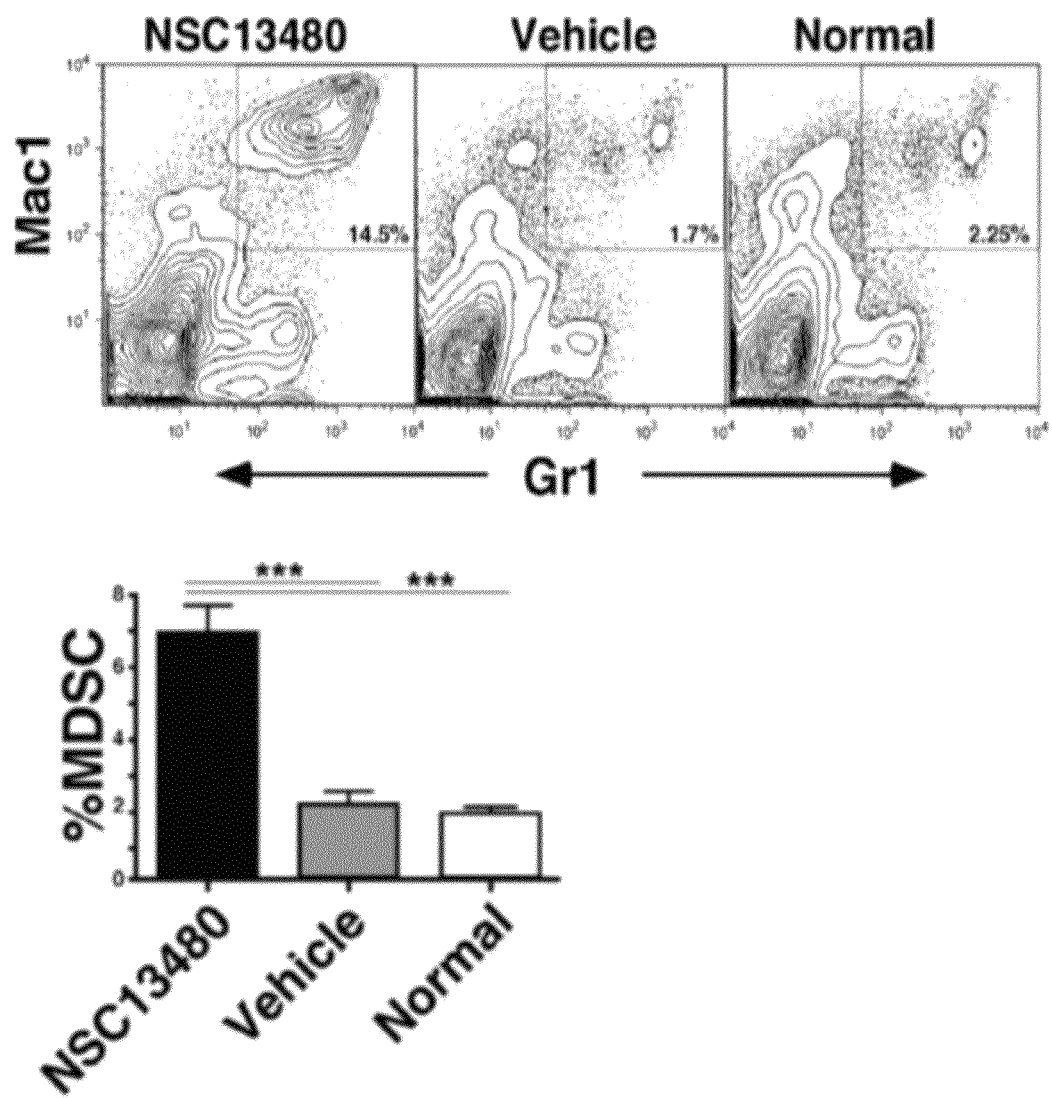
FIG. 10 shows treatment with the SHIP inhibitor, NSC13480, expands the myeloid and T lymphoid immunoregulatory compartment in secondary lymphoid tissues. FACS quantitation of Mac1$^+$Gr1$^+$ Myeloid-Derived Suppressor Cells (Mac1$^+$Gr1$^+$ MySC) (A,B) and FoxP3$^+$CD4$^+$CD25$^+$ Treg cells (C,D) in spleen and lymph node of C57BL6 mice treated with NSC13480, vehicle or non-manipulated mice (Normal). ***$p<0.001$; *$p<0.05$.
Figure 10B:
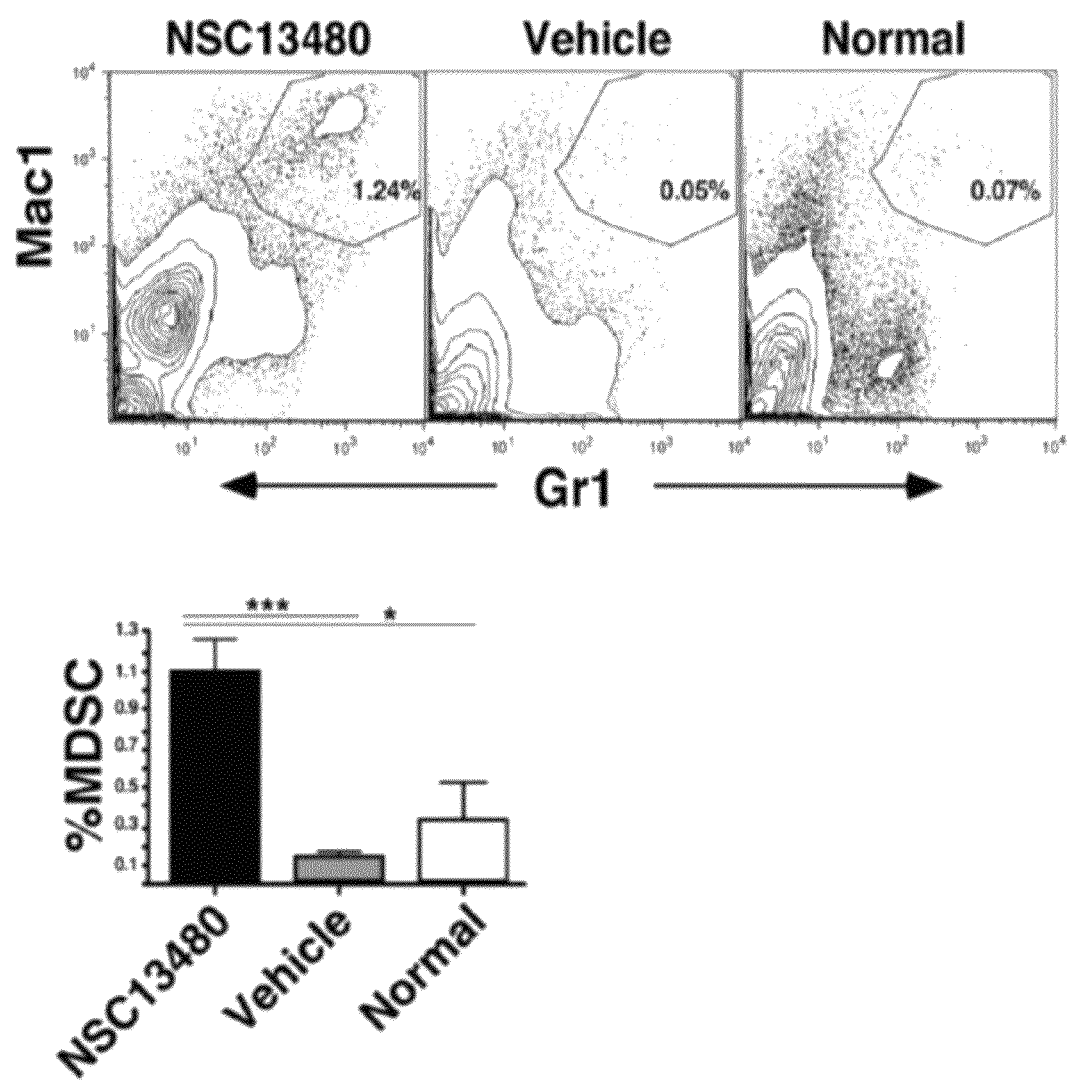
Figure 10C:
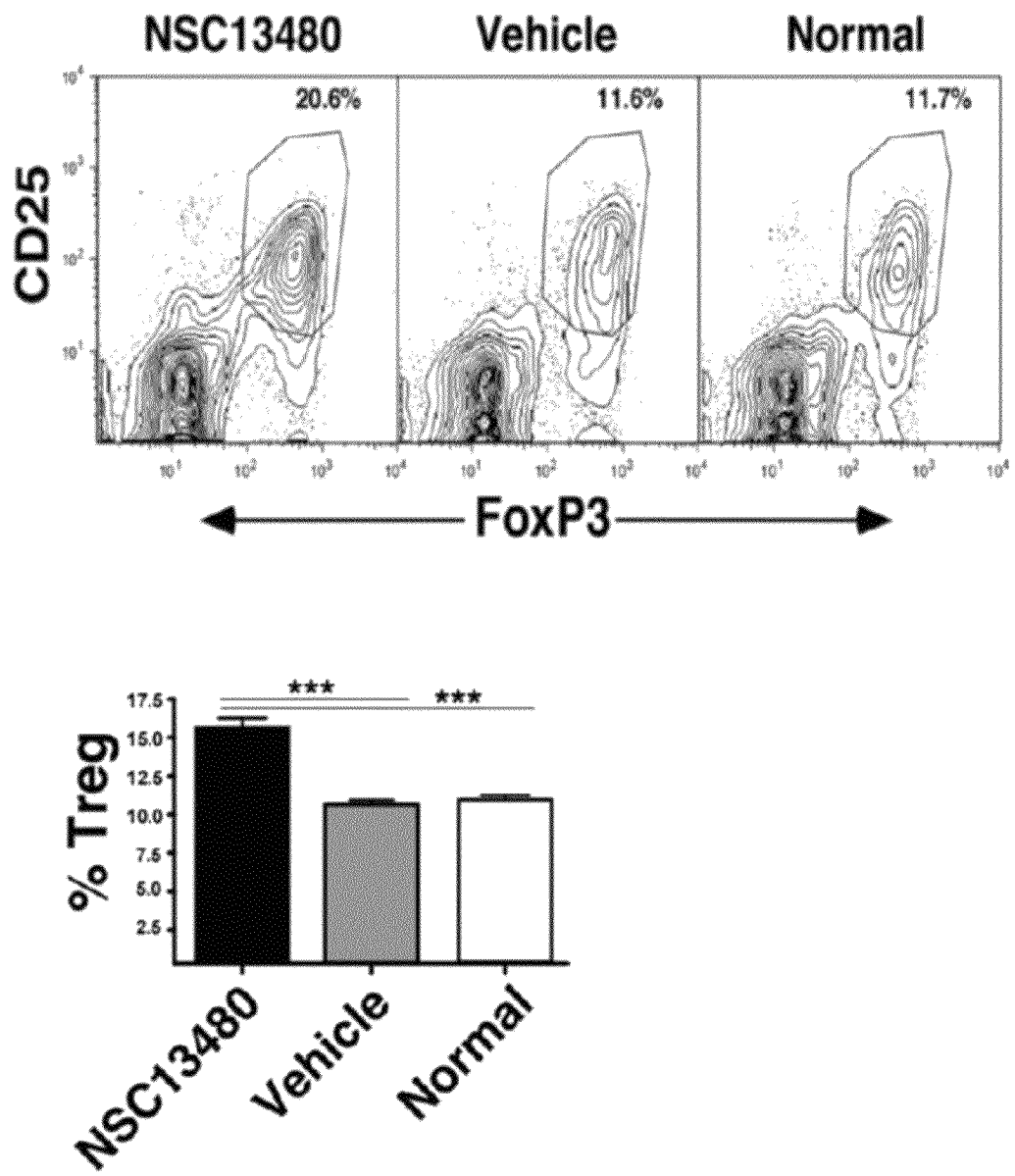
Figure 10D:
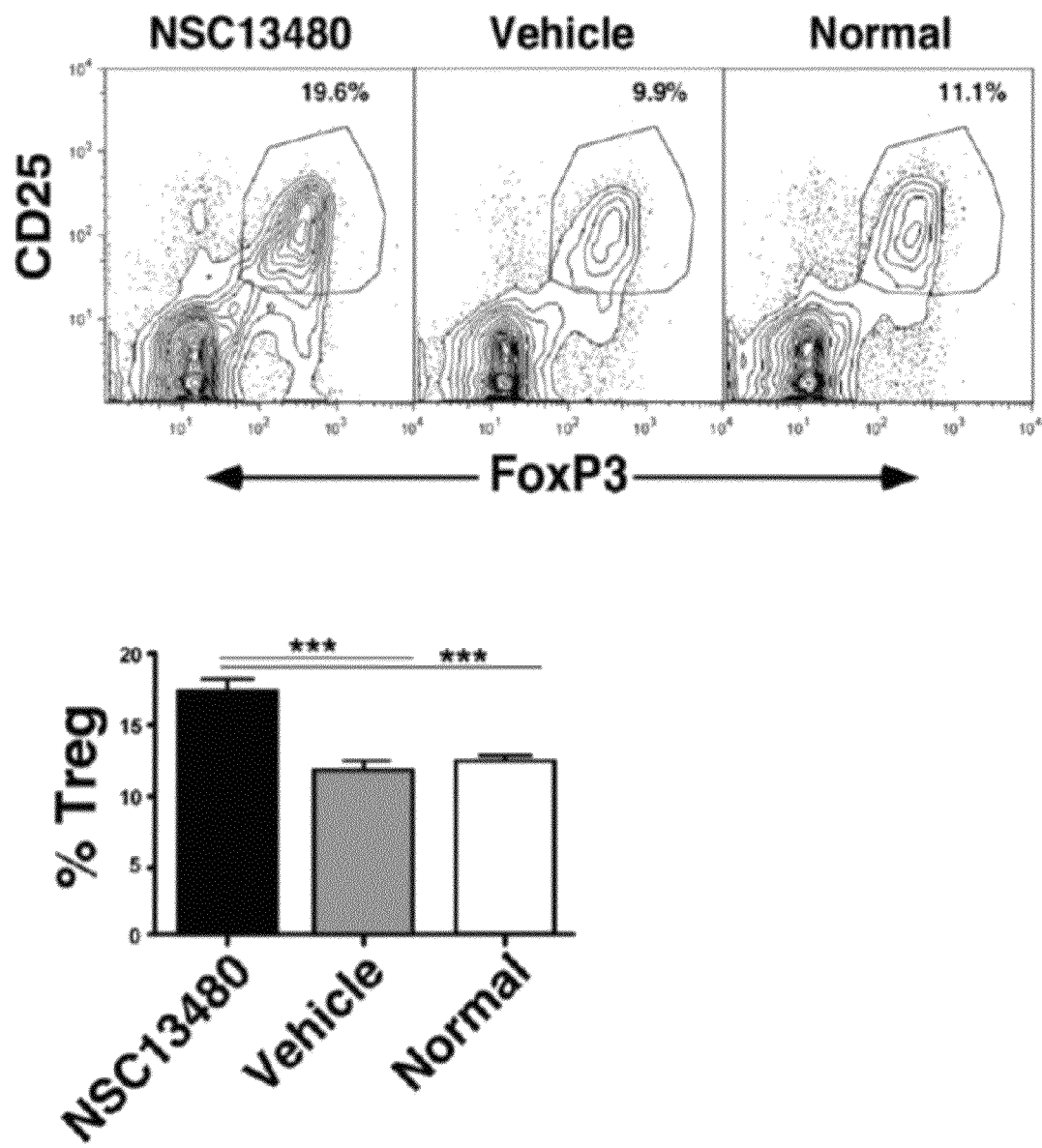

In Vivo Treatment with a SHIP Inhibitor Expands the MySC and Treg Cell Compartments in Secondary Lymphoid Tissues Myeloid suppressor cells (MySC) have been shown to suppress graft-versus-host disease (GvHD) [Ghansah, T., et al., *J Immunol* (2004)173:7324; Paraiso, K. H., et al., *J Immunol* (2007)178:2893]. In addition, both donor and host Treg cells can also limit or abrogate GvHD. MySC numbers are substantially increased following induction of SHIP-deficiency in adult mice, and, moreover, SHIP-deficient MySC are more potent at suppressing allogeneic T cell responses than their WT counterparts. (Paraiso, K. H., et al. 2007. *J Immunol* 178:2893). It was found that induction of SHIP-deficiency in adult mice also increases the number of CD4$^+$CD25$^-$ Treg numbers in both spleen and LN as well as increases the number of FoxP3 expression in naive/effector CD4$^+$CD25$^-$ T cells allowing them to adopt immunoregulatory behavior (Collazo and Kerr, unpublished data). Thus, the ability of one of the more potent SHIP inhibitors, NSC13480, was tested for its ability to expand the myeloid and T lymphoid immunoregulatory cell compartments in secondary lymphoid tissues where GvHD is primed. Adult mice were treated for 7 days with a daily injection of NSC13480 at 125 µM. The frequency of MySC and Treg cells was tested in the spleens of mice treated with NSC13480, the vehicle used for delivery of NSC 13480 and normal, untreated mice. The number of myeloid-derived suppressor cells (MDSC; Mac1$^+$Gr1$^+$ MySC), (see FIGS. 10a and 10b), and Treg cells (FIGS. 10c and 10d), are increased significantly in both spleen (FIGS. 10a and 10c) and LN (FIGS. 10b and 10d) following a one week regimen of daily NSC13480 injections.

Example 5

Figure 11:
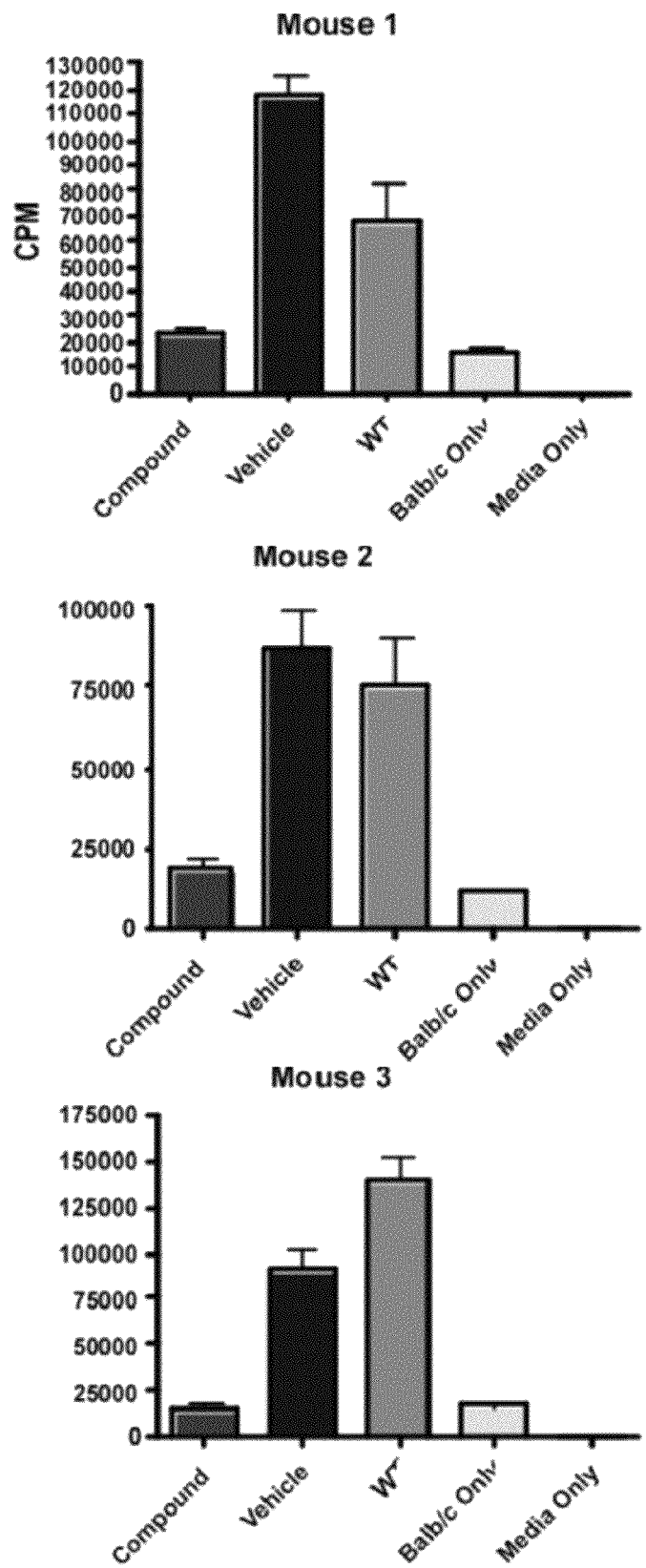
FIG. 11 shows in vivo SHIP inhibition impairs the ability of peripheral lymphoid tissues to prime allogeneic T cell responses.

Peripheral Lymphoid Tissues from SHIP Inhibitor Treated Mice Prime Allogeneic T Cell Response Very Poorly Based upon the results discussed above, the expansion of both the MySC and Treg cell compartments in the peripheral lymphoid tissues, as induced by NSC13480, was also expected to create an immunosuppressive environment, particularly for priming of allogenic T cell responses. To assess this possibility, splenocytes were tested from NSC13480-treated mice for their ability to prime an allogeneic T cell response by responder T cells that are completely MHC mismatched. The results are presented in FIG. 11. As shown in the figure, there was profound inhibition of allogeneic T cell priming observed when splenocytes from three NSC13480 treated mice were used as stimulators, while robust priming of allogeneic T cells was observed with splenocytes from either vehicle treated mice or normal mice. Thus, chemical inhibition of SHIP's enzymatic activity in vivo expands two different immunoregulatory cell compartments in peripheral lymphoid tissues and, consistent with this expansion, impairs the ability of these tissues to properly activate allogeneic T cells.

Example 6

Figure 12A:
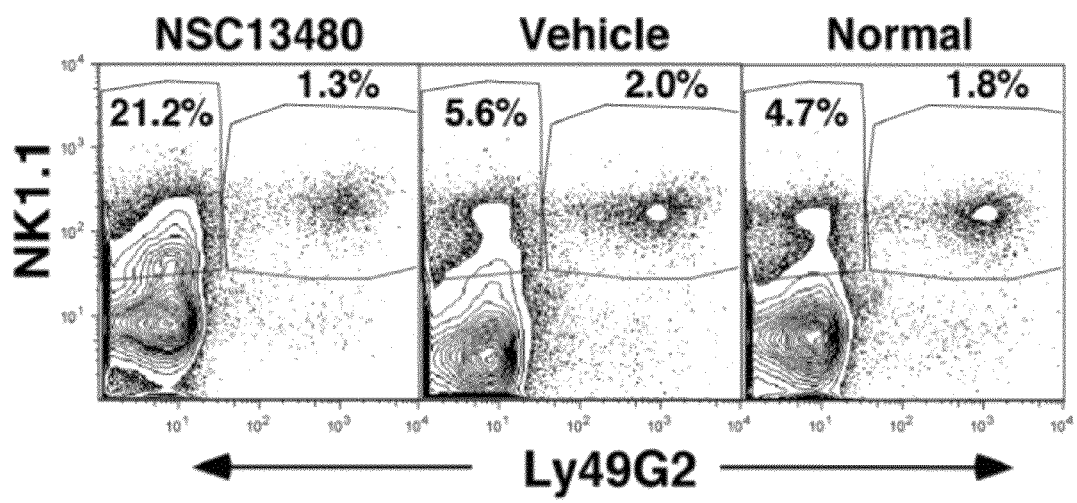
FIG. 12 shows the SHIP inhibitor NSC13480 increases peripheral NK cell numbers and alters the NK receptor repertoire. Mice were treated daily for 6 days with either NSC13480, vehicle alone (Vehicle) or were non-manipulated (Normal). On the 7th day the spleens of the mice were analyzed for NK cell content (NK1.1+CD3– cells) and for expression of the MHC-I inhibitory receptor Ly49G2. Consistent with previous findings in SHIP–/– mice (Wang et al Science 2002), chemical inhibition of SHIP activity significantly increased the percentage of NK cells in the periphery (A., B.) and significantly decreased the representation of Ly49G2 in the peripheral NK compartment (A., C.). *$p<0.0001$, $p<0.01$, *$p<0.05$.
Figure 12B:
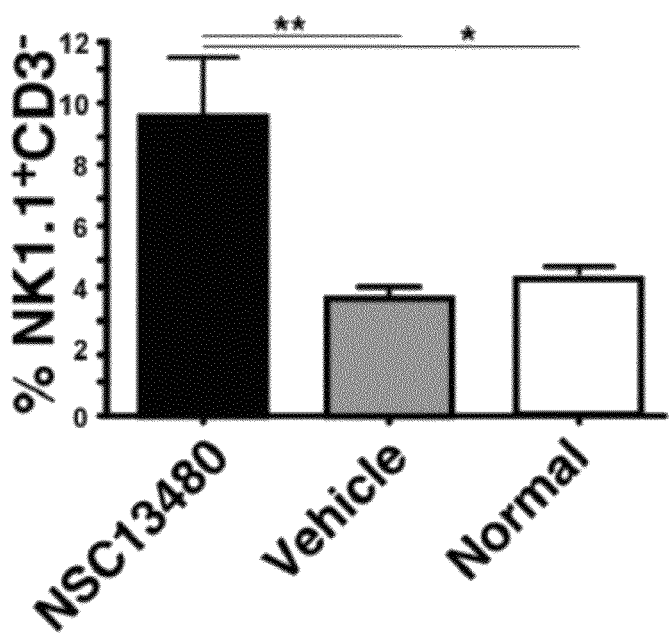
Figure 12C:
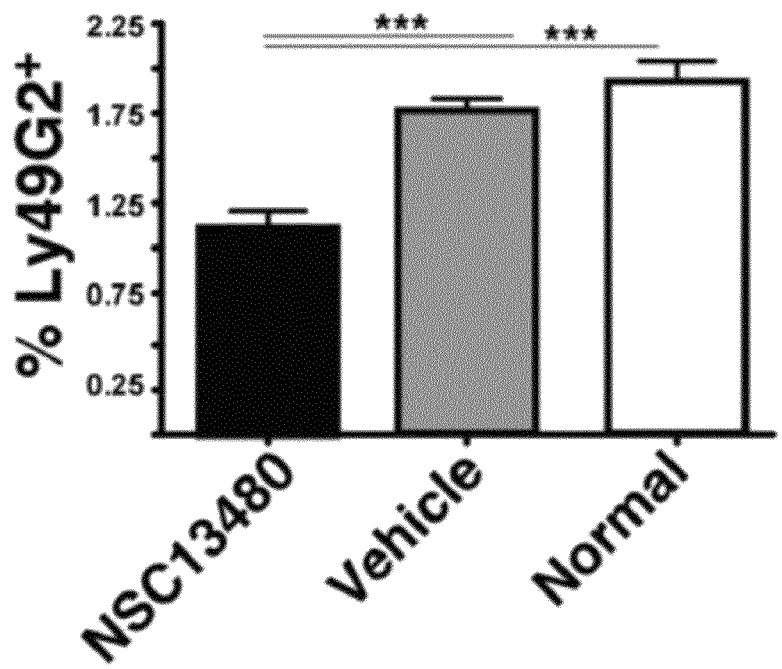

SHIP Inhibition Increases Peripheral NK Cell Numbers and Alters the Representation of Inhibitory MHC-I Receptors SHIP-deficiency expands the peripheral NK compartment and disrupts the repertoire of receptors elaborated by NK cells that recognize MHC-I ligands. The NK cell compartment was examined in NSC13480-treated mice to determine if inhibition of SHIP enzymatic activity in vivo could also lead to similar disruptions in the NK cell compartment. Indeed, NSC13480-treated mice were found to exhibit a significant increase in splenic NK cell numbers, but have a much reduced frequency of Ly49G2$^+$ NK cells. Ly49G2 is an MHC-I inhibitory receptor shown to be under-represented in SHIP$^{-/-}$ mice. These results are presented in FIG. 12.

Example 7

A High-Throughput Screen (HTS) Identifies a SHIP1 Selective Inhibitor

Figure 15:
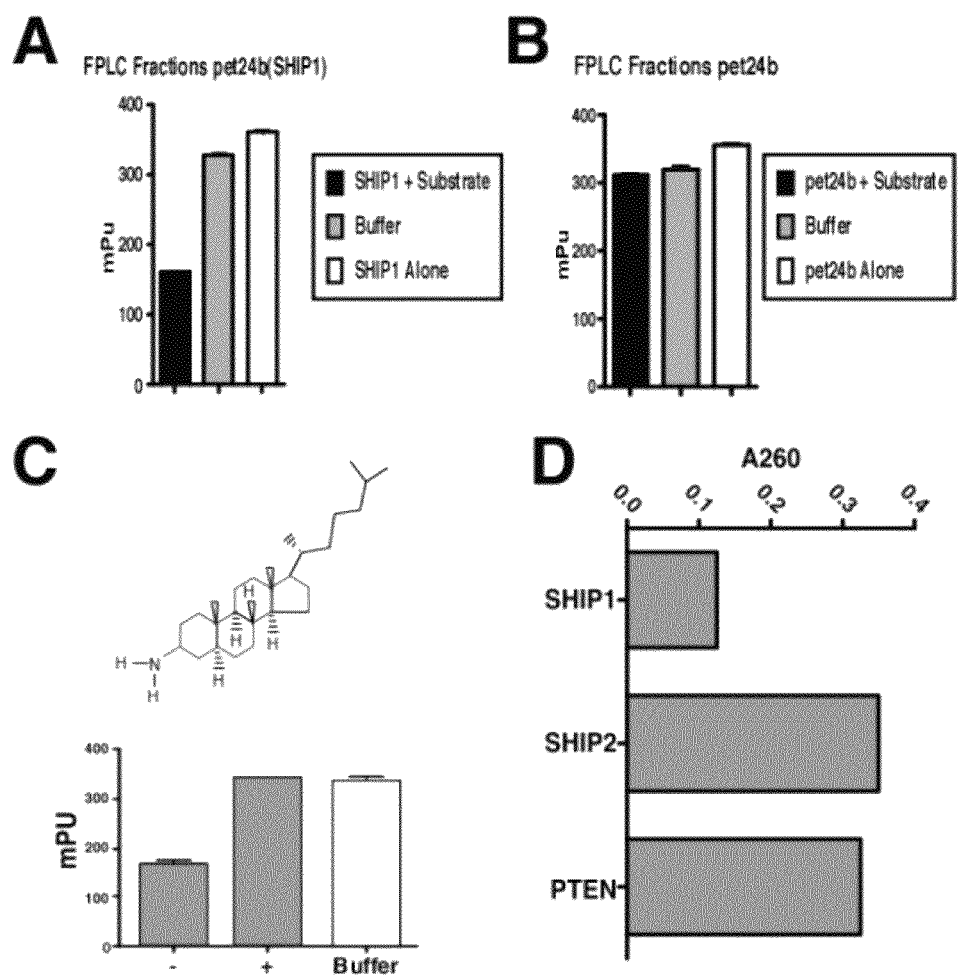
FIG. 15 shows SHIP1 expression, purification and the identification of a chemical inhibitor of SHIP1. (A) Purified, recombinant SHIP1 has significant activity as determined by the reduction in mean polarization units (mPu) in an FP assay designed for 5'-inositol phosphatases (Echelon Biosciences, Salt Lake City, Utah.). Note that no significant reduction in mP is obtained when the enzyme buffer without SHIP1 is added to the FP assay (Buffer) or when purified SHIP1 is assayed in the absence of its PI(3,4,5)P3 substrate (SHIP1 only). (B) FP assay on FPLC fractions which were prepared from E. coli that harbor an 'empty' pET24b vector and which show no reduction in mP indicating there is no detectable 5'-inositol phosphatase activity present in comparable FPLC fractions prepared from the same E. coli host that does not express SHIP1. (C) 3α-aminocholestane (see structure) inhibits SHIP1 activity at 100 µM in the FP assay. (D) 3α-aminocholestane fails to inhibit SHIP2 or PTEN activity at 1 mM as measured by the Malachite Green assay that detects phosphate release. Absorbance levels for SHIP2 and PTEN in the presence of 1 mM 3α-aminocholestane were equivalent to that seen with a fully hydrolyzed substrate control, while the absorbance levels for SHIP1 at 1 mM were equivalent to a control reaction where no substrate was added indicating full inhibition.

A fluorescence polarization (FP) assay to detect and quantify SHIP2 activity has been previously described [Drees B E, et al., *Comb Chem High Throughput Screen* (2003) 6(4):321-330], but no assay has been described for the detection of SHIP1. A fluorescence polarization (FP) assay was developed to detect the activity of recombinant SHIP1 (see FIGS. 15a and b) and the FP assay was utilized as a rapid screen to detect compounds in chemical libraries that have inhibitory activity against SHIP1. This screen identified 3α-aminocholestane as a potent inhibitor of SHIP1 enzymatic activity (FIG. 15c). Using the FP assay, it is found that that 3α-aminocholestane exhibits detectable inhibitory activity against 0.1 µg of recombinant SHIP1 at 2 µM and 50% inhibition at 10 µM. To determine whether 3α-aminocholestane exhibits selectivity for SHIP1, its capacity to inhibit SHIP2 and PTEN, the other two SH2-containing inositol phosphatases in the mammalian cell (both of which also hydrolyze the PI3K product, PI(3,4,5)P$_3$), was assessed. It was found that 3α-aminocholestane is selective for SHIP1, as it fails to inhibit SHIP2 and PTEN at 1 mM (FIG. 15d). This high degree of selectivity could be important, since loss of PTEN function promotes malignancy in parenchymal and hematopoietic tissues. [Yuan T L & Cantley L C *Oncogene* (2008) 27(41):5497-5510; Zhang J, et al., *Nature* (2006) 441(7092):518-522; Yilmaz O H, et al., *Nature* (2006) 441(7092):475-482]

Example 8

SHIP1 Inhibition Promotes the Expansion of the Myeloid Immunoregulatory Cell and Granulocyte Compartments Expansion of the Mac1$^+$Gr1$^+$ MIR cell compartment can suppress GvHD. [Ghansah T, et al., *J Immunol* (2004) 173 (12):7324-7330; Paraiso K H, et al., *J Immunol* (2007) 178 (5):2893-2900; MacDonald K P, et al., *J Immunol* (2005) 174(4):1841-1850] Thus, the ability 3α-aminocholestane to expand the MIR compartment in peripheral lymphoid tissues, where GvHD and organ transplant rejection are primed, was tested. Adult mice were treated for 7 days with a daily intraperitoneal (i.p.) injection of 3α-aminocholestane at 60 µM. We then compared the frequency of MIR cells in the spleens and LN of mice treated with 3α-aminocholestane to that of control mice treated with either their respective vehicles or to unmanipulated mice. It was found that the number of MIR cells is increased significantly in both spleen (FIG. 16a) and LN (FIG. 16b) following treatment with 3α-aminocholestane. No significant increase in MIR cells was observed with vehicle treatment relative to unmanipulated controls. Thus, consistent with the findings in mice genetically ablated for SHIP1 expression during adult physiology [Paraiso K H, et al., *J Immunol* (2007) 178(5):2893-2900], inhibition of SHIP1 activity in adult mice expands the MIR cell compartment in peripheral lymphoid tissues.

Increased numbers of MIR cells in peripheral lymphoid tissues of germline SHIP1-deficient mice, and in mice where SHIP1 expression is genetically ablated during adulthood, impairs priming of allogeneic T cell responses. [Ghansah T, et al., *J Immunol* (2004) 173(12):7324-7330; Paraiso K H, et al., *J Immunol* (2007) 178(5):2893-2900] The peripheral expansion of the MIR cell compartment promoted by 3α-aminocholestane should then promote an immunosuppressive environment, particularly for priming of allogeneic T cell responses. To assess this possibility, splenocytes from H2b mice treated with 3α-aminocholestane were tested for their ability to prime allogeneic T cell responses by completely mismatched H2d responder splenocytes. Their responses were compared to splenocytes from either unmanipulated mice or splenocytes from mice treated with vehicle. The results showed that splenocytes from mice treated with 3α-aminocholestane are profoundly impaired in their ability to stimulate allogeneic T cell responses (FIG. 16c). Thus, chemical inhibition of SHIP1 enzymatic activity in vivo expands potent immunoregulatory cell populations in peripheral lymphoid tissues and, consistent with this expansion, these tissues are profoundly compromised for priming of allogeneic T cell responses. The ability of 3α-aminocholestane to inhibit priming of a human allogeneic T cell response in vitro was also examined. It was found that pre-treatment of human PBMC significantly reduces their ability to prime allogeneic responses by T cells from an unrelated donor (FIG. 16d). Thus, SHIP1 inhibition significantly reduces priming of human or rodent allogeneic T cell responses.

It has recently been shown that SHIP1-deficient mice exhibit increased G-CSF production [Hazen A L, et al., *Blood* (2009) 113(13):2924-2933]. Accordingly, we tested whether the chemical inhibition of SHIP1 leads to increased production of myeloid cells like granulocyte/neutrophils, analogous to the effect of recombinant G-CSF administration in cancer patients. To test this, granulocyte levels were measured after a week of daily treatment with 3α-aminocholestane. Treatment with 3α-aminocholestane led to a 5- to 6-fold increase in circulating granulocytes in peripheral blood relative to either vehicle or unmanipulated controls (FIG. 16e). Wright-Giemsa staining of cytosmears prepared from the blood of the treated mice confirmed the granulocyte increase had a neutrophil morphology (data not shown). Intriguingly, this profound expansion of circulating granulocyte numbers following 3α-aminocholestane treatment occurs in the absence of the pulmonary myeloid infiltration and lung consolidation that is uniformly lethal for adult SHIP1$^{-/-}$ mice (FIG. 16f).

[Ghansah T, et al., *J Immunol* (2004) 173(12):7324-7330; Helgason C D, et al. (1998) *Genes & Development* 12(10: 1610-1620] Thus, chemical inhibition of SHIP1 can profoundly enhance granulocyte/neutrophil output without causing the lung consolidation and pneumonia that limits the lifespan of germline SHIP1$^{-/-}$ mice.

Example 9

SHIP1 Inhibition Promotes Apoptosis and Reduces Growth of Leukemia Cells

Figure 17A:
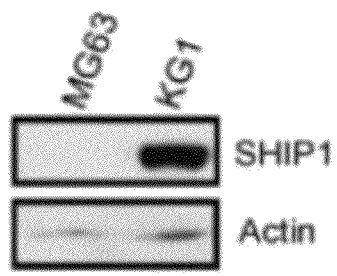
FIG. 17 shows that SHIP1 inhibition decreases the growth and survival of AML cells in vitro. (A) SHIP1 expression in KG1 and MG63 cells was determined by Western blotting (top). Membranes were reprobed with antibodies against b-actin to confirm equal loading (lower panel). One representative blot of 2 individual experiments is shown. (B) KG1 and MG63 cells were plated in duplicate in 96 well plates, and treated for 36 hours with increasing concentrations of the 3α-aminocholestane. Cell viability was assessed by MTT assay. Results represent the mean of three individual experiments. (C) KG1 cells were treated with increasing concentrations of 3α-aminocholestane for 36 hours and hallmarks of apoptosis were identified in cell lysates by Western Blot analysis. Membranes were probed with antibodies against PARP and cleaved PARP (cPARP, upper panel) and cleaved Caspase 3 (cCaspase 3, middle panel). Equal protein loading was confirmed by reprobing the blots with anti-b-actin antibodies (lower panel). A representative example of 2 independent experiments is shown. (D) KG1 cells were treated with increasing concentrations of 3α-aminocholestane, and the percentage of AnnexinV and PI positive cells was determined by FACS analysis. A representative example of 2 individual experiments is shown.
Figure 17B:
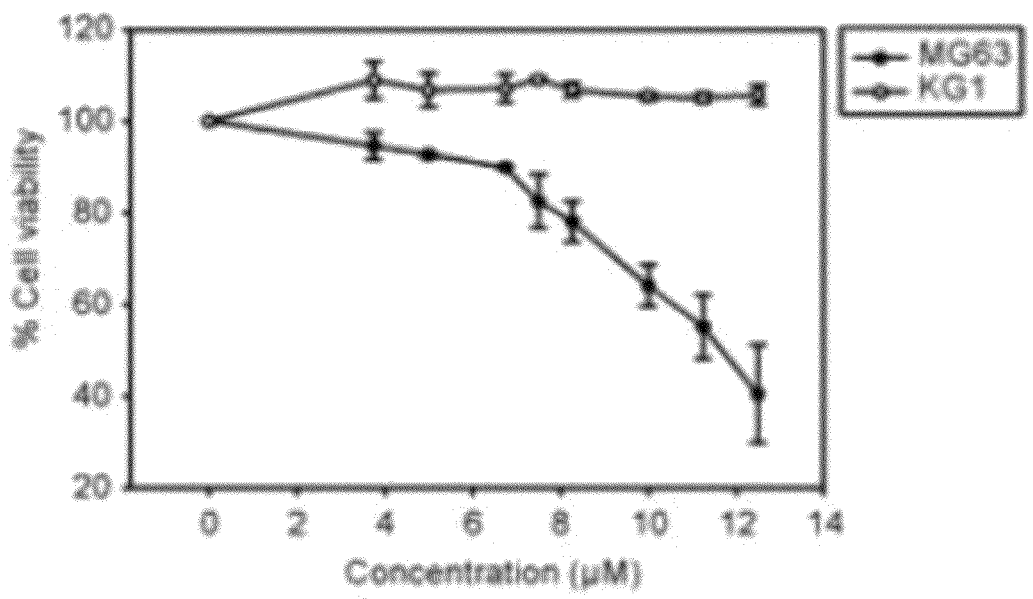
Figure 17C:
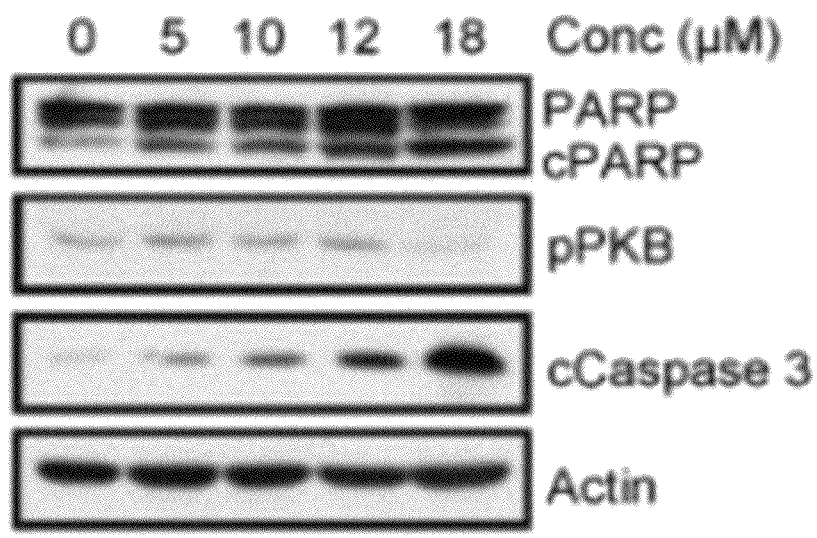
Figure 17D:
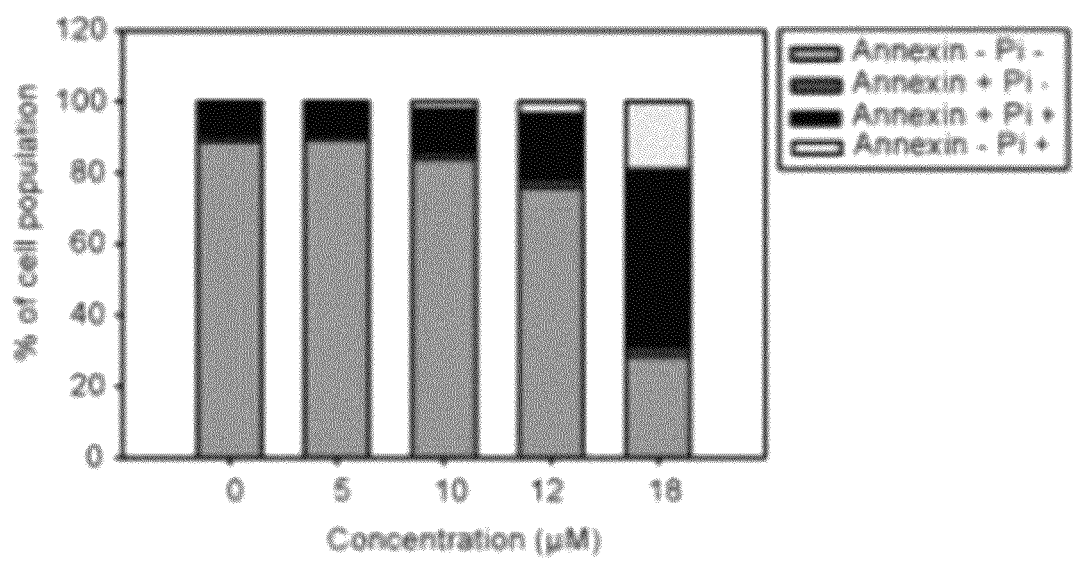
Figure 18A:
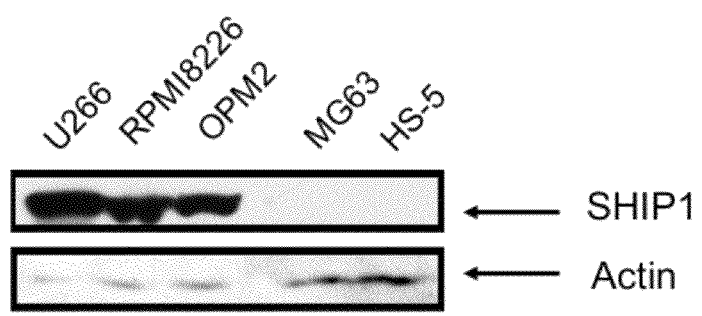
FIG. 18 shows the inhibition of human multiple myeloma cell lines by a SHIP inhibitor. (A) SHIP1 expression in human multiple myeloma (MM) cell lines as presented in the western blot analysis. SHIP is expressed in the human multiple myeloma cell lines U266, RPMI8226 and OPM2. The expression in the MM cell lines is shown relative to that observed in MG63 and HS-5 cell lines. MG63 is an osteosarcoma cell line, and HS-5 is a human bone marrow stroma cell line. The data show that neither of these non-MM lines expresses SHIP. Actin is provided as a control. (B) Results of MTT dye assays of MM cell lines. A decrease in viability of three multiple myeloma cell lines was observed in the presence of increasing concentrations of "Comp 5", referred to in the specification as the SHIP inhibitor NSC23922 or 3α-aminocholestane. RUO is "relative units optical". (C) Apoptosis in OPM and RPMI cell lines at increasing concentrations of 3α-aminocholestane. The data presented in the graph shows that apoptosis occurs in two human multiple myeloma cell lines, OPM and RPMI, exposed to Comp 5 (i.e. NSC23922/3α-aminocholestane), with the percent annexin positive cells indicative of the fraction of cells undergoing apoptosis, or programmed cell death.
Figure 18B:
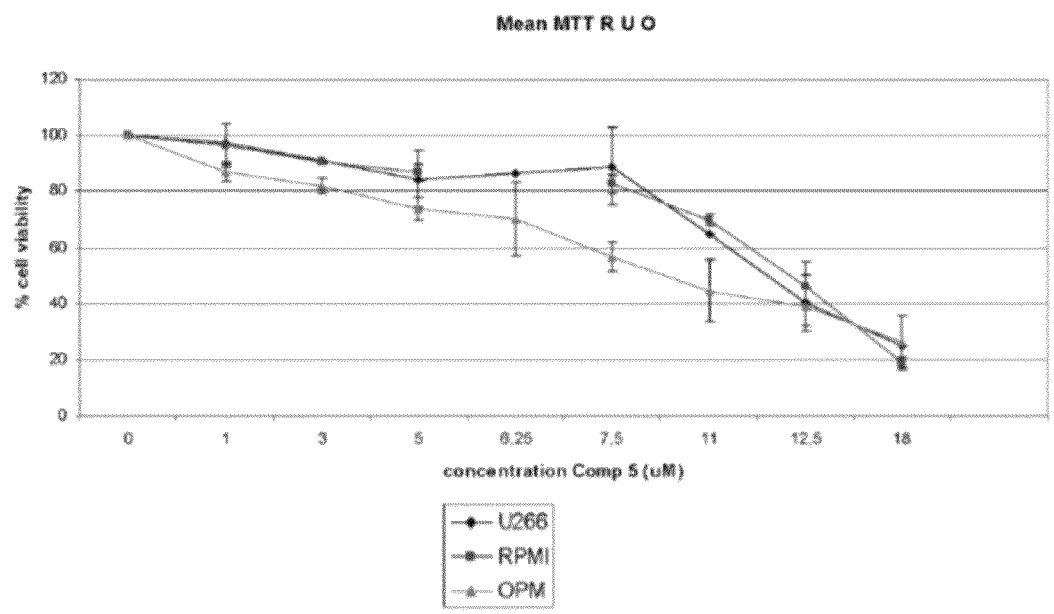
Figure 18C:
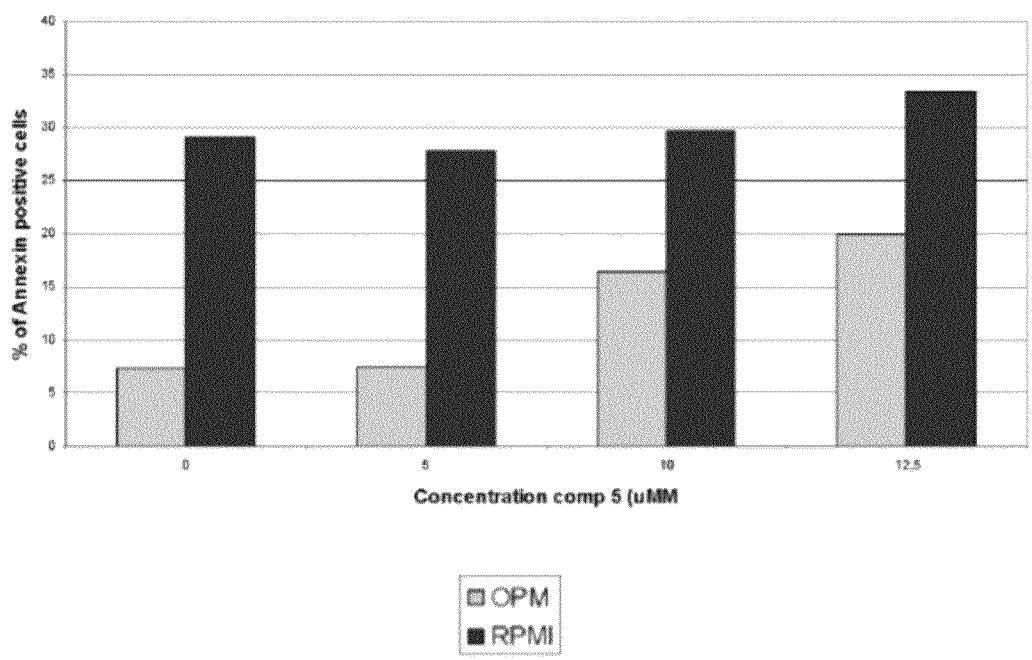
Figure 19A:
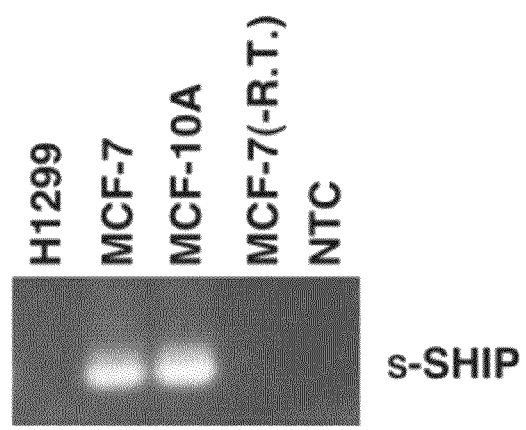
FIG. 19 shows the expression of a variant of SHIP that is found in stem cells, s-SHIP, in human breast cancer cell lines (mammary epithelial cells and transformed mammary epithelial cells). The observed expression implicates that the SHIP inhibitors of the invention have application in the treatment of breast cancer. (A) RT-PCR analysis of s-SHIP expression in the indicated cell lines ("NTC" is No Template Control; "-R.T." is Minus Reverse Transcriptase control), which shows that s-SHIP is expressed in the human breast cancer cell line MCF-7 and the normal mammary epithelial line MCF-10A, but not in the human non-small cell lung cancer line H1299. s-SHIP is an isoform of SHIP that is expressed in stem cells (see Tu et al., *Blood* (2001) 96(7)2028-38). The data suggest that inhibitors of SHIP could inhibit cancer stem cells, giving rise to cancer cells, that express s-SHIP. FIG. B is the raw RT-PCR data showing the quantification of SHIP in MCF-7 and MCF-10A cells.
Figure 19B:
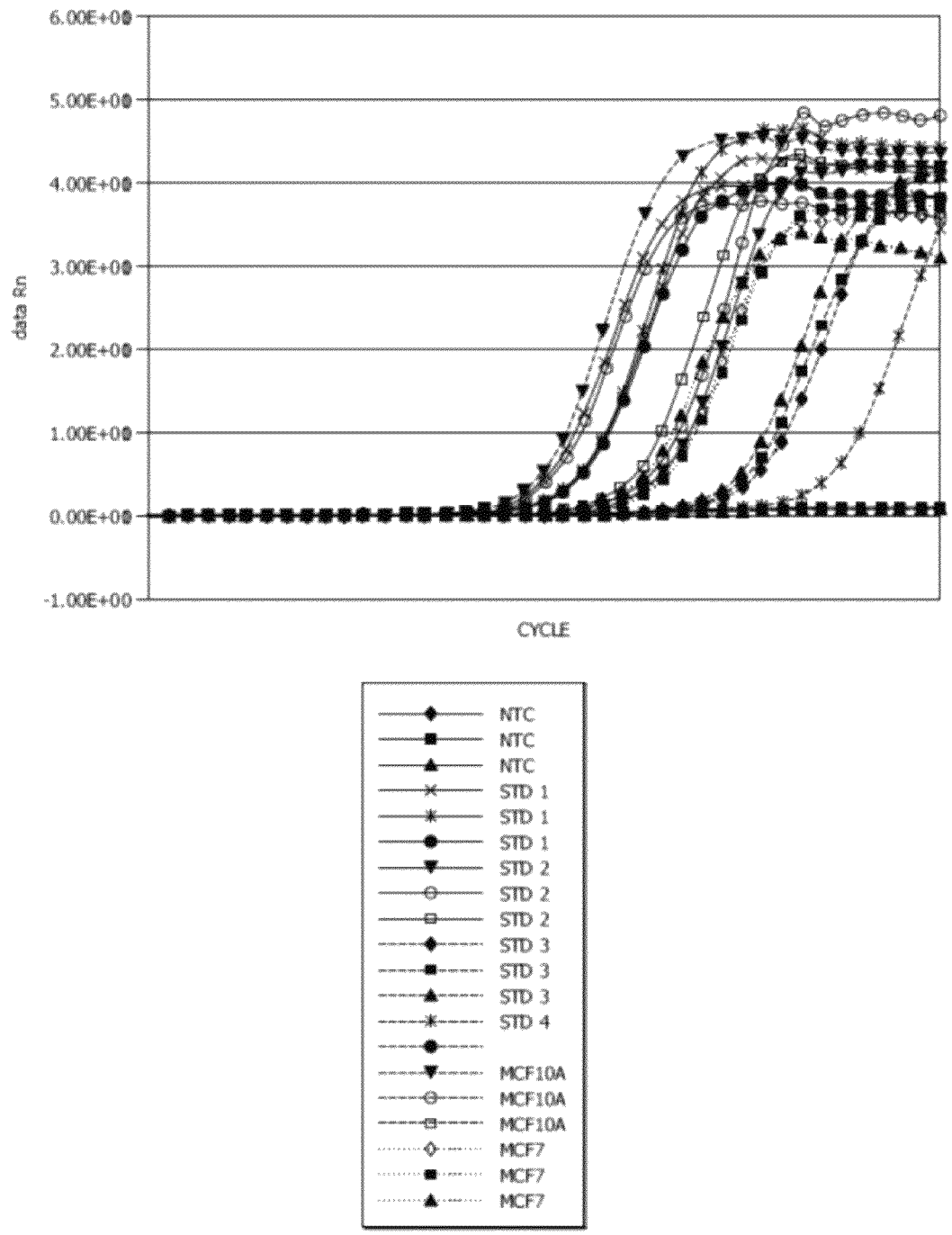

It was a concern that SHIP1 inhibitors might potentially enhance the survival and growth of blood cell cancers. Conversely, as discussed above, SHIP1 inhibition could also decrease Akt activation and therefore might also antagonize the survival of malignant blood cells. The two possibilities were tested by treating the AML cell line (KG-1) that expresses SHIP1 (FIG. 17a) with 3α-aminocholestane. It was found that 3α-aminocholestane decreases the growth and survival of KG-1 AML cells in vitro, but not in cells that lacks SHIP1 expression (FIG. 17a, b). It was also found that 3α-aminocholestane promotes apoptosis of SHIP-expressing AML cells based on increased cleavage of PARP and Caspase 3, decreased activation of Akt/PKB and increased frequency of AnnexinV$^+$ cells (FIG. 17c, d). Thus, SHIP1 inhibition can reduce the growth and survival of certain forms of human blood cell cancer.

Materials and Methods

Compounds tested in the models were obtained from the NCI.

Mouse strains: C57BL6/J and BALB/C mice were purchased from Jackson Laboratories.

Antibody staining and flow cytometry (Examples 1-6): Anti-CD16/32 was co-incubated with the samples to block Fc receptor binding. Antibodies used for staining included: NK1.1 (PK136); CD3e (145-2C11); Ly49G2 (4D11); Gr-1 (RB6-8C5); Mac-1(M1/70); CD11c (HL3); CD4 (GK1.5); CD25 (PC61) and were obtained from BD Pharmingen (San Jose, Calif.). FoxP3 (FJK-16s) was purchased from eBio-Science (San Diego, Calif.). All samples were acquired on a FACSCalibur and analyzed using FlowJo8.7.1. For viable staining, dead cells were excluded from the analysis following cytometer acquisition of data by exclusion of the 7AAD dye. For staining of FoxP3, viable cells were first stained for extacellular markers followed by fixation and permeabilization to stain for the intracellular FoxP3.

MLR studies: Both direct addition and prior treatment was used in MLR studies.

Expression and purification of recombinant SHIP1: A SHIP1 cDNA expression construct was amplified by PCR from the pMIGR1(SHIP1) vector [Tu Z, et al., *Blood* (2001) 98(7):2028-2038] and then inserted into the pET24b bacterial expression vector at the EcoR1 and Xho1 restriction sites in this vector to create a SHIP1-His tag fusion at the C-terminus. His-tagged SHIP1 was then expressed in *E. coli* Rosetta-Gami 2 (DE3) pLys cells by induction following the addition of 0.5 mM IPTG and purified by Ni-chelating bead chromatography.

Assay of SHIP1 enzymatic activity: A fluorescent polarization (FP) assay that detects the 5'-inositol phosphatase activity of SHIP1 was developed based on a previously established protocol [Drees B E, et al., *Comb Chem High Throughput Screen* (2003) 6(4):321-330] and was obtained from Echelon Biosciences (Salt Lake City, USA). Modifications of the protocol included the application of SHIP1 in the assay and an increase in the concentration of MgCl$_2$ to 20 nM to maximize the activity of SHIP1 in this assay. Each enzymatic reaction was performed in a 96 well working plate and added in the following order and concentration: Recombinant SHIP1 (0.1 µg) in PBS+20 mM MgCl$_2$, 100 µM of each individual compound from the NCI Diversity Set and then PI(3,4,5)P$_3$ substrate diluted 1:10 in H$_2$O. The enzymatic reaction was incubated for 30 min at room temperature. The detector, reaction mixture and probe were then combined according to the SHIP2 protocol. Malachite Green Phosphatase Assay Kit was obtained from Echelon Biosciences (Salt Lake City, USA). Assays for SHIP2 were performed according to the manufacturer's protocol. The concentration of SHIP1 and SHIP2 per reaction mixture was 0.02 n/ml. PTEN was used at the concentration recommended by the manufacturer.

Use of SHIP1 inhibitory compounds for in vitro and in vivo studies: For in vitro studies 3α-aminocholestane was suspended in 100% ethanol. For in vivo studies 3α-aminocholestane was suspended in a 0.3% Klucel/H$_2$O solution at 11.46 mM. Vehicle treated mice received a 200 µl injection of 0.3% Klucel/H$_2$O solution. The final concentration of 3α-aminocholestane in the treated mice was 60 µM For in vivo both vehicle and compound treated mice received daily i.p. injections for seven days prior to analysis or tissue harvest.

Antibody staining and flow cytometry (Examples 7-9): Anti-CD16/32 was incubated with the samples to block Fc receptor binding. Antibodies used for staining included: Gr-1 (RB6-8C5) and Mac-1(M1/70) and were obtained from BD Pharmingen (San Jose, Calif.). All samples were acquired on a FACSCalibur and analyzed using FlowJo8.7.1. For viable staining, dead cells were excluded from the analysis following cytometer acquisition of data by exclusion of the 7AAD dye.

Mixed leukocyte reactions (MLR): Following RBC lysis, irradiated (2000 Rads) BL6 splenocytes (stimulators) at 8×10$^5$ cells/well were combined with BALB/c splenocytes (responders) at 4×10$^5$ cells/well in a one-way MLR assay. All cells were plated in sextuplicate in a 96-well U-bottom plate (Falcon) containing RPMI 1640 complete medium for 4 days. Cells were then pulsed with 1 µCi of [3H]thymidine/well for 18 hr. Cells were lysed and high M.W. DNA captured on glass fiber filtermates using an automated cell harvester (Packard Instruments). Incorporated [3H]thymidine was quantitated using a Packard TopCount NXT. Specific [3H]thymidine incorporation into genomic DNA was calculated as the average of the mean (±SEM) of sextuplicate wells. For the human MLR studies, human PBMC to be used as stimulators were first cultured at 4×10$^6$ cells/ml for 24 hr in human IL15 medium [RPMI medium, 10% FBS, 20 mM HEPES, Pen/Strep, L-Glutamine, non-essential amino acids, 20 mM 2ME supplemented with human IL15 (10 ng/ml)] containing either 9.4 µM 3α-aminocholestane or vehicle. The 3α-aminocholestane- or vehicle-treated stimulator PBMC (8×10$^5$ cells) were then mixed with responder PBMC (4×10$^5$ cells) from a different donor in 200 µl of human IL15 medium. Four days later 1 µCi [3H]thymidine was added to the wells and 18 hr later cells were harvested, lysed and high M.W. DNA captured on glass filtermates. Specific [3H]thymidine incorporation into genomic DNA was calculated as the average of the mean cpm (±SEM) of sextuplicate wells.

Cell culture: The Acute Myeloid Leukemia cell line KG1 was obtained from ATCC (Manassas, Va.) and was cultured in Dulbecco's Modified Eagle Medium (DMEM) (Invitrogen, Carlsbad, Calif.) supplemented with 100 U/mL penicillin, 100 µg/mL streptomycin (Invitrogen, Carlsbad, Calif.) and 20% fetal calf serum (PAA, Etobicoke, Ontario, Canada). MG63 cells were a kind gift from Dr R. van Bezooyen (LUMC, Leiden, The Netherlands), and were propagated in DMEM containing 100 U/mL penicillin, 100 µg/mL streptomycin and 10% fetal calf serum.

Preparation of cell lysates and Western blotting: Cells were counted, centrifuged and resuspended in Laemmli sample buffer. SDS-PAGE and immunoblotting were performed according to standard procedures. Detection was performed according to the manufacturer's guidelines (ECL, Pierce, Rockford, Ill.). Membranes were probed with antibodies against Phospho-Akt Ser473, Cleaved PARP, Cleaved Caspase 3 (Cell Signaling Technology, Beverly, Mass.) or SHIP1 (Santa Cruz Biotechnology Inc, Santa Cruz, Calif.). To confirm equal loading, membranes were reprobed with an antibody against β-actin (Santa Cruz Biotechnology).

Cell viability assay: Cells were treated in duplicate for 36 hours with increasing concentrations of 3α-aminocholestane or vehicle. 3-(4,5-Dimethylthiazol-2-yl)-2,5diphenyltetrazolium bromide (MTT) (Sigma, St Louis, Mo.) was added at a concentration of 0.5 mg/ml to the cells for 3 hours. Formed crystals were dissolved in dimethyl sulfoxide and optical density (OD) was measured at 570 nm. The OD of compound treated cells was divided by the OD of their vehicle control, and the viability was expressed as a percentage of untreated cells. Results are expressed as mean±SEM of three individual experiments.

Annexin V staining Annexin V/Propidium Iodide (PI) staining was performed using the Annexin V-FITC apoptosis detection kit from BD Pharmingen (Sharon, Mass.) per the manufacturer's instructions. In short, cells were treated with increasing concentrations of 3α-aminocholestane for 36 hours. Cells were harvested, washed twice with ice-cold PBS and stained with Annexin-FITC and PI in binding buffer for 15 minutes. Fluorescence was determined by flow cytometry (LSR II, Becton Dickinson Medical Systems, Sharon, Mass.).

All references cited in the present application are incorporated in their entire herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of inhibiting inositol 5-phosphatase (SHIP) in a subject having multiple myeloma, wherein said method comprises administering an effective amount of 3α-aminocholestane (NSC 23922) to said subject in need thereof, wherein SHIP is inhibited by said administration.

* * * * *